United States Patent [19]

Christensen et al.

[11] 4,318,912

[45] Mar. 9, 1982

[54] 6-(1-HYDROXYETHYL)-3-SUBSTITUTED-1-AZABICYCLO(3.2.0)-HEPT-2-EN-7-ONE-2-CARBOXYLIC ACID

[75] Inventors: Burton G. Christensen, Scotch Plains; Ronald W. Ratcliffe, Matawan, both of N.J.

[73] Assignee: Merck & Co., Inc., Rahway, N.J.

[21] Appl. No.: 160,717

[22] Filed: Jun. 18, 1980

Related U.S. Application Data

[63] Continuation-in-part of Ser. No. 470, Jan. 2, 1979, abandoned, which is a continuation of Ser. No. 843,620, Oct. 19, 1977, abandoned.

[51] Int. Cl.$^3$ .................. C07D 487/04; A61K 31/40; C07D 213/55
[52] U.S. Cl. .................................. 424/263; 424/274; 546/272; 260/245.2 T
[58] Field of Search ................. 260/245.2 T; 546/272; 424/274, 272, 269, 266, 263

[56] References Cited

U.S. PATENT DOCUMENTS 4,232,036 11/1980 Christensen et al. ............... 424/274
4,235,917 11/1980 Christensen et al. ............... 424/274
4,235,920 11/1980 Christensen et al. ............... 424/274

Primary Examiner—Alan L. Rotman
Attorney, Agent, or Firm—Hesna J. Pfeiffer; James A. Arno

[57] ABSTRACT

Disclosed are 6-(1'-hydroxyethyl)-3-substituted-1-azabicyclo[3.2.0]hept-2-en-7-one-2-carboxylic acids(I):

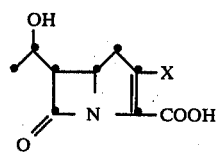

wherein X is halo, oxygen (the 2-3 bond is saturated and the species I exists as the carboxylate salt or ester), or —OR wherein R is, inter alia, acyl, alkyl or aralkyl. Such compounds and their O- and carboxyl derivatives are useful as antibiotics. Also disclosed are processes for the preparation of such compounds, pharmaceutical compositions comprising such compounds and methods of treatment comprising administering such compounds and compositions when an antibiotic effect is indicated.

4 Claims, No Drawings

6-(1-HYDROXYETHYL)-3-SUBSTITUTED-1-AZABICYCLO(3.2.0)-HEPT-2-EN-7-ONE-2-CARBOXYLIC ACID

BACKGROUND OF THE INVENTION

This is a continuation-in-part of U.S. Ser. No. 000,470 filed Jan. 2, 1979 abandoned, which is a continuation of U.S. Ser. No. 843,620 filed Oct. 19, 1977, now abandoned.

This invention relates to 6-(1'-hydroxyethyl)-3-substituted-1-azabicyclo[3.2.0]hept-2-en-7-one-2-carboxylic acids and their pharmaceutically acceptable salt, ester and amide derivatives (I) which are useful as antibiotics:

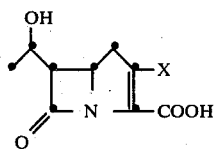

wherein X is oxygen (the 2-3 bond is saturated and the species I exists as the carboxylate salt or ester), halo, or —OR wherein R is, inter alia, acyl, alkyl or aralkyl. The radical R is more fully defined below. It should be noted that species wherein X is O exhibit enol-keto tautomerism and thus X may also be —OH.

This invention also relates to the O- and/or carboxyl derivatives of I which are antibiotics and which may be represented by the following generic structure (Ia):

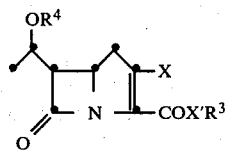

wherein X' is oxygen, sulphur or NR' (R'=H or lower alkyl having 1-6 carbon atoms); and $R^3$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below; $R^4$ is (1.) acyl (generically the group $OR^4$ is classifiable as an ester); or (2.) $R^4$ is selected from alkyl, aryl, aralkyl and the like (such that the group $OR^4$ is generically classifiable as an ether). The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyle, sulfinyl-, and sulfenyl-radicals, and substituted P (III and V) radicals such as substituted phosphorous-, phosphoric-, phosphonous- and phosphonic-radicals, respectively. Such acyl radicals of the present invention are further defined below, as are the radicals (2., above) which constitute the ether embodiments of the present invention.

This invention relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microroganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. Aureus, Strep. pyogenes. B. subtilis* and gram negative bacteria such as *E. coli, Proteus morganii,* Pseudomonas, Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The preparation of the compounds (I) of the present invention may conveniently be summarized by the following reaction diagram:

$$H_2C=CHCH=CHOR^1 + OCNSO_2Cl \longrightarrow$$

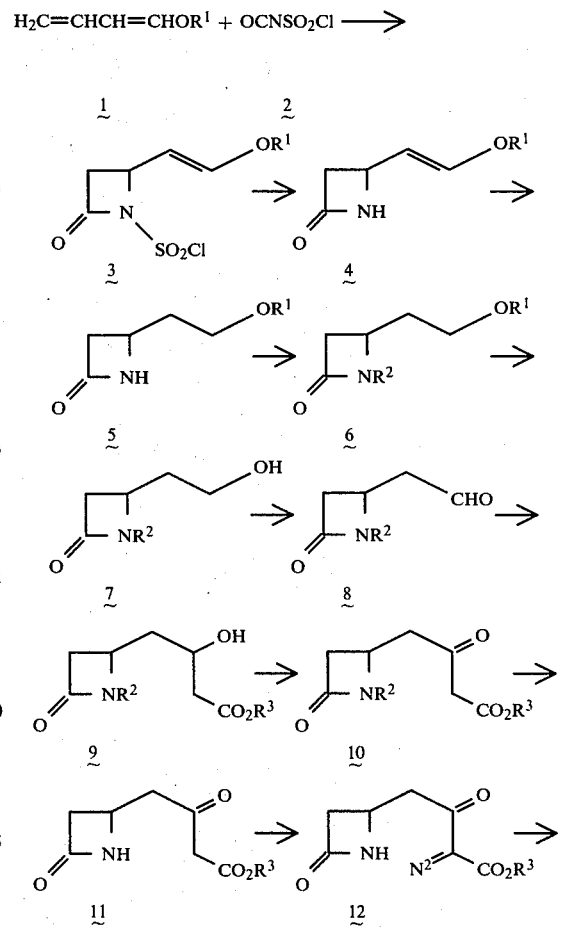

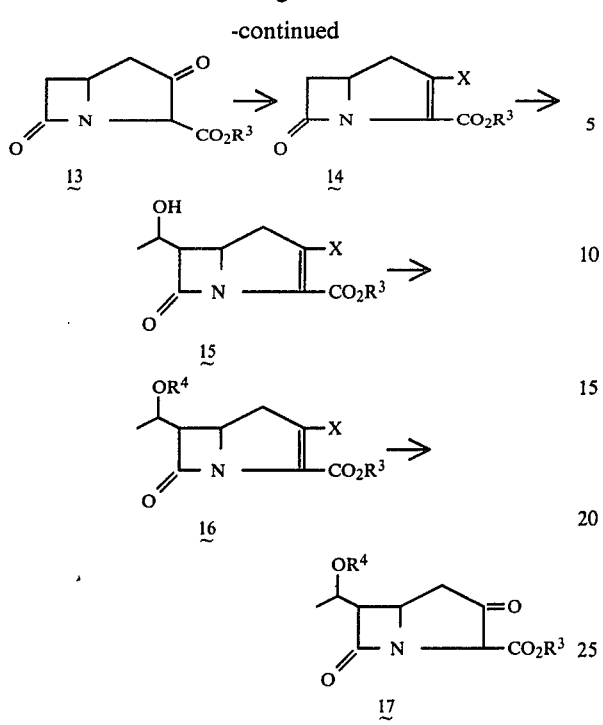

In words relative to the above reaction diagram starting materials 4 and 8 and the reaction sequence 1→→8 are disclosed in co-pending, commonly assigned U.S. Patent Application Ser. No. 792,071 filed Apr. 28, 1977; this application, as it relates to these starting materials, is incorporated herein by reference. Basically, however, the 4-(2-substituted-vinyl)azetidine-2-one, 4 starting material is prepared by reacting an $R^1$-oxybutadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical $R^1$ is an easily removable acyl blocking group such as an alkanoyl or aralkanoyl which bears no functional group or groups which might interfere with the desired course of reaction (1+2→3→4). Intermediate species 3 is converted to the sulfinamide by reduction which is then hydrolyzed to 4 at pH 6–8. Typically the reaction solution comprising 3 is contacted (5–30 minutes) with an aqueous solution (at 0°–25° C.) of a reducing agent such as sodium sulfite, thiophenol, or the like, at pH 6–8 to provide 4.

The reaction 4→5 is a reduction, and is preferably achieved by hydrogenation in a solvent such as ethyl acetate, ether, dioxane, tetrahydrofuran(THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The reaction 5→7 establishes, if desired, the N-protecting group $R^2$, which preferably is a cyclic ether such as 2-tetrahydropyranyl or a triorganosilyl radical, such as trimethylsilyl or t-butyl-dimethylsilyl. Alternatively, $R^2$ may be hydrogen. Typically, when the protecting group $R^2$ is a triorganosilyl radical, such as t-butyldimethylsilyl, species 5 in a solvent such as dimethylformamide(DMF), dioxane, tetrahydrofuran(THF), diethylether(Et$_2$O) or the like in the presence of a base such as triethylamine, imidazole, pyridine, hexamethyldisilazane or the like is contacted with the desired silylating agent such as t-butyldimethylsilylchloride, trimethylsilylchloride, isopropyldimethylsilylchloride or the like at a temperature of from −10° to 40° C. for from 10 minutes to 8 hours. Suitable reagents for the establishment of $R^2$ when $R^2$ is a cyclic ether such as 2-tetrahydropyranyl, 2-methoxy-2-tetrahydropyranyl, 4-methoxy-4-tetrahydropyranyl or the iike are: 2,3-dihydro-4H-pyran, 6-methoxy-2,3-dihydro-4H-pyran, 4-methoxy-5,6-dihydro-2H-pyran and the like. The establishment of such cyclic ether protecting groups is typically conducted in a solvent such as Et$_2$O, EtOAc, dioxane, DMF and the like in the presence of an acid, such as HCl, p-toluenesulfonic acid, or phosphoryl chloride at a temperature of from 0° to 25° C. for from 10 minutes to 3 hours.

The deblocking reaction 6→7 is preferably accomplished by alcoholysis wherein the solvent is a lower-alkanol such as methanol, ethanol or the like in the presence of the corresponding alkali metal alkoxide, such as sodium methoxide. Typically, the reaction is conducted for from 5 minutes to 3 hours at a temperature of from −10° to 25° C.

The aldehyde intermediate 8 is prepared by treating 7 with an oxidizing agent such as CrO$_3$.2 (pyridine) in CH$_2$Cl$_2$, 1:1 mixture of dimethylsulfoxide (DMSO) and acetic anhydride, pyridinium chlorochromate in CH$_2$Cl$_2$, dicyclohexylcarbodiimide in DMSO, methylene chloride or the like at a temperature of from 0°–25° for from 5 minutes to 8 hours.

The condensation of the aldehyde to provide species 9 (8→9) is accomplished by treating 8 in a solvent such as Et$_2$O, THF, (hexamethylphosphoramide) HMPA or the like at a temperature of from −78° to 0° C. for from 1 minute to 1 hour in the presence of a base such as lithium diisopropylamide, KH or the like with an ester of acetic acid (CH$_3$CO$_2$R$^3$; wherein $R^3$ is a readily removable carboxyl protecting group or a pharmaceutically acceptable ester moiety; suitable values for $R^3$ are defined below).

Intermediate ketone species 10 is obtained by oxidation of 9 following the previously described oxidation procedure 7→8. The N-protecting group $R^2$ is easily removed by mild acid hydrolysis such as acetic acid in water at a temperature of from 25° to 100° C. for from 1 to 20 hours to provide species 11 (10→11).

The diazo species 12 is prepared from 11 by treating 11 in a solvent such as CH$_3$CN, CH$_2$Cl$_2$, THF and the like with an azide such as p-carboxybenzenesulfonylazide, toluene sulfonylazide, methanesulfonylazide and the like in the presence of base such as triethylamine, pyridine, (C$_2$H$_5$)$_2$NH and the like for from 1 to 50 hours at 0° to 25° C.

Cyclization of the diazo compound to provide 13 (12→13) is preferably accomplished by irradiating through a pyrex filter (λ greater than 300 nm) in a solvent such as φH, φMe, THF, or the like at a temperature of from 50° to 110° C. for 1–5 hours in the presence of a catalyst such as bis(acetylacetonato) Cu(II) [Cu(acac)$_2$], CuSO$_4$, Cu powder, Rh(OAc)$_2$, or Pd(OAc)$_2$. Species 13 may also be prepared according to the disclosure found in European Patent Application No. 79101307.1 (filed May, 1, 1979), Publication No. 007973/A1, which is incorporated herein by reference, when the incorporated, disclosed procedure omits the alkylation schemes which establish the hydroxyethyl moiety, Step 7→8.

The reaction 13→14 establishes the group X which group may be as hereinabove described or it may be a readily removable protecting group such as a triorganosilyloxy group such as trimethylsilyloxy, t-butyldimethylsilyloxy or the like.

Basically, relative to species 14, when X is OR wherein R is an acyl group (see below for definition), 14 is prepared by reacting 13 in a solvent such as benzene, CH$_2$Cl$_2$, THF, DMF and the like in the presence of a base such as Et$_3$N, pyridine, 4-dimethylaminopyridine, propylene oxide and the like at a temperature of from 0° to 25° C. with a reagent calculated to introduce the acyl radical, R, of choice. Generically, such acylating agent may be selected from the following list of reagents, acid chlorides

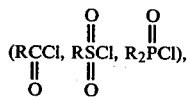

acid anhydrides ((RCO)$_2$O, (RSO$_2$)$_2$O), ketenes, activates acid esters and the like. Representative examples of such reagents are: ketene, acetic anhydride, acetyl chloride, azido acetyl chloride, phenyl acetyl chloride, benzoic anhydride, benzoyl chloride, propionic anhydride, diphenyl ketene, p-nitrophenyl chloroacetate, N-benzyloxycarbonyl glycyl chloride, methanesulfonyl chloride, p-toluenesulfonyl chloride, p-toluenesulfonic anhydride. Species 14 wherein X is OR and R is other than acyl, which species may generically be classified as ethers, are conveniently prepared from 13 by treating 13 with a diazo reagent calculated to provide the radical R in a solvent such as Et$_2$O, CH$_2$Cl$_2$, CH$_3$OH, CH$_3$CN, benzene and the like at a temperature of from 0° to 80° C. for from 15 minutes to 2 hours. Representative examples of such diazo reagents are: diazomethane, 1-diazobutane, 3-propyl-1-p-tolyltriazene, 3-ethyl-1-p-tolyltriazene, 3-benzyl-1-p-tolyltriazene, phenyl diazomethane, diphenyldiazometahne, and the like.

The ether derivatives are also obtained by alkylating keto ester intermediate 13 with an alkylating agent RX such as CH$_3$SO$_3$F, (CH$_3$)$_2$SO$_4$, or TsOCH$_2$CH$_2$N$_3$ (X is a leaving group, and Ts=tosyl) in a solvent such as (CH$_3$)$_2$CO or HMPA in the presence of a base such as K$_2$CO$_3$, sodium hydride, potassium t-butoxide or the like at a temperature of from −20° to 40° C. for from 0.5 to 3 hours. When R is a readily removable blocking group such as triorganosilyl radical, the species 14 is most conveniently prepared by treating 13 in the presence of a base such as triethylamine, imidazole, pyridine and the like in a solvent such as Et$_2$O, φH, THF and the like with a triorganosilyl chloride such as trimethylsilyl chloride at a temperature for from 0° to 25° C. for from 0.5 to 5 hours.

When X is a halo group, 14 is prepared by treating 13 with a halogenating agent such as PCl$_3$, SOCl$_2$, POCl$_3$, (COCl)$_2$, PBr$_3$, SOBr$_2$ or the like in a solvent such as DMF, CHCl$_3$, φH or the like for from 0.5 to 8 hours at 0° to 80° C.

Preferred reagents and conditions for preparation of the 3-chloro species are PCl$_3$ or SOCl$_2$ in a solvent such as DMF at a temperature of 0° to 25° C. for from 1 to 6 hours; for 3-bromo species the conditions are the the same using PBr$_3$ or SOBr$_2$.

Regardless of the identity of the X radical of species 14, species 14 is converted to species 15 by alkylating with acetaldehyde in the presence of a base such as lithium diisopropylamide, lithium cyclohexyl isopropylamide, KH, NaNH$_2$, and the like in a solvent such as Et$_2$O, THF, HMPA, glyme, DMF, DMSO and the like at a temperature of from −78° to 0° C. for from 1 minute to 1 hour. The reaction 15→16 to derivatize the 1'-hydroxyethyl group by establishment of the radical R$^4$ is discussed below. Conversion of 16→17 when X is a readily removable blocking group such as triorganosilyloxy is conveniently accomplished by mild acid hydrolysis. Species 15, 16 and 17 may also be prepared according to the disclosure found in European Patent Application No. 79101307.1 filed May, 1, 1979), Publication No. 007973/A1, which is incorporated herein by reference.

It should be noted that all intermediate species may be carboxyl deblocked (when R$^3$ is a readily removable blocking group) by mild aqueous hydrolysis or hydrogenolysis.

Alternatively, the 6-(1'-hydroxyethyl) side chain may be established by the alkylation of a suitably protected azetidinone intermediate in the above-defined reaction scheme, so that the aldehyde intermediate azetidinone 8 bears the desired 1'-hydroxyethyl side chain. The following reaction diagram summarizes this alternative scheme:

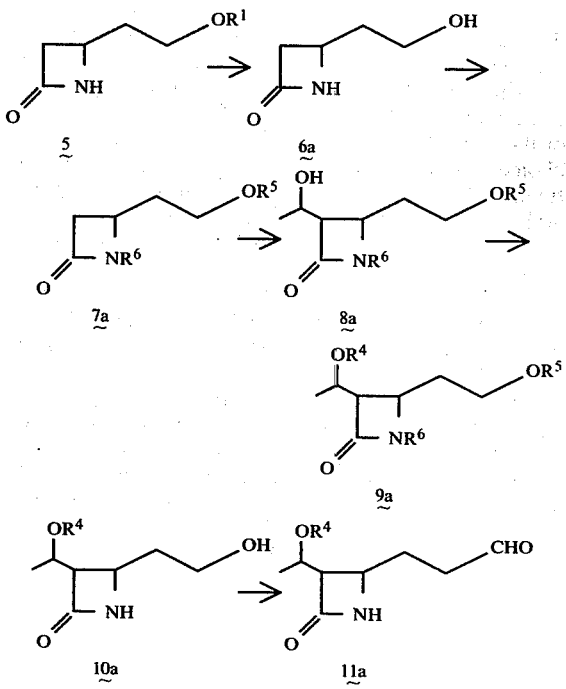

Relative to the above reaction diagram, it will be noted that intermediate species 11a ties into the first reaction scheme at intermediate species 8 and that all reactions subsequent to species 8 in the first reaction diagram apply in an analogous way to species 11a. Further, in words relative to the above reaction diagram species 5 may be deblocked to form species 6a by mild aqueous hydrolysis depending upon the identity of R$^1$.

Blocking groups R$^6$ and R$^5$ are established 6a→7a to provide a suitably protected species for alkylation 7a→8a. There is no criticality in the choice of blocking groups, provided only that they do not interfere with the intended alkylation. R$^6$ may be hydrogen, a triorganosilyl group such as trimethylsilyl or the like, or a cyclic ether such as 2-tetrahydropyranyl; $R^5$ may also be a cyclic ether such as 2-tetrahydropyranyl; alternatively $R^6$ and $R^5$ may be joined together to form protected species such as 7a:

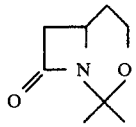

For example, species such as 7a are conveniently prepared by treating 6a with 2,2-dimethoxypropane in the presence of a catalyst such as boron trifluoride etherate, toluene sulphonic acid, or the like in a solvent such as methylene chloride, ether, chloroform, dioxane or the like at a temperature of from $-10°$ C. to 35° C. for from a few minutes to 1 hour.

The alkylation 7a→8a is preferably conducted by treating 7a with a strong base such as lithium diisopropylamide, sodium amide, potassium hydride or the like in a solvent such as THF, glyme, ether, dimethylformamide (DMF), dimethylsulfoxide (DMSO) or the like at a temperature of from $-78°$ C. to $0°$ C. The resulting anion is then treated with excess acetaldehyde to provide 8a.

The reaction 8a→9a establishes the blocking group $R^4$ and is typically accomplished by treating 8a with a base such as an alkali metal hydroxide, lithium diisopropyl amide 4-dimethylaminopyridine, or n-butyllithium in a solvent such as ether, THF, dioxane, DMF, DMSO or the like, followed by treatment with an acyl halide of choice such as an alkanoyl, aralkanoyl or nuclear substituted aralkanoyl, or alkyl, aryl or aralkyl, substituted aralkyl or substituted aryl haloformate such as p-nitrobenzylchloroformate or the like at a temperature of from $-78°$ to 25° C. for from 1-24 hours.

The de-blocking reaction 9a→10a is typically conducted by acid hydrolysis such as aqueous acetic acid at a temperature of from 25° C. to 75° C. for form 5 minutes to 3 hours.

The aldehyde intermediate 11a is prepared by treating 10a with an oxidizing agent such as $CrO_3.2$(pyridine) in $CH_3CN$, 1:1 mixture of dimethylsulfoxide and acetic anhydride, dicyclohexylcarbodiimide in DMSO or the like at a temperature of from 0°–25° C. for from 5 minutes to 1 hour.

IDENTIFICATION OF THE RADICAL X

In the generic description of the compounds of the present invention (I):

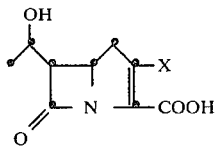

X is oxygen, halo, such as bromo or chloro, or —OR wherein R is selected from the group consisting of substituted and unsubstituted: alkyl, having 1–6 carbon atoms, cycloalkyl and cycloalkylalkyl wherein the ring moiety comprises 3–6 carbon atoms and the alkyl moiety comprises 1–4 carbon atoms, aralkyl having from 7–16 carbon atoms, and acyl; wherein the substituent or substituents on the radical R are selected from: amino; mono-, di- and trialkylamino wherein the alkyl has 1–6 carbon atoms; alkoxyl having 1–6 carbon atoms; chloro, bromo; amidino; guanidino; and carboxyl. Generically, the term "acyl" as it relates to the definition of R is inclusive of the alkanoyls including derivatives and analogues thereof such as thio analogues wherein the carbonyl oxygen is replaced by sulphur; as well as sulphur and phosphorous acyl analuges such as substituted sulfonyl-, sulfinyl-, and sulfenyl-radicals, and substituted P(III and V) radicals such as substituted phosphorous-, phosphoric-, phosphonous- and phosphonic-radicals, respectively. Such acyl radicals of the present invention are further defined below.

Representative of such acyl radicals, R, are:

wherein X is O and S or R' (or R'') is: OR'', NR$_2$'', SR'', substituted or unsubstituted alkyl having 1–6 carbon atoms, aryl such as phenyl, aralkyl such as benzyl or phenethyl, or heterocycle wherein the hetero atom or atoms are selected from oxygen, sulfur and nitrogen. More specifically suitable acyl radicals, R, are:

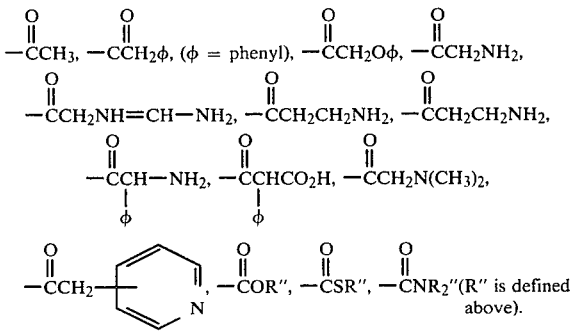

The radical R may also be

wherein R' is as defined above;

wherein R' is as defined above; and

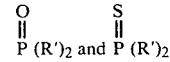

wherein R' is —OR'' or —NR$_2$''.

Relative to the definition of the compounds of the present invention (I) the most preferred values for the radical R are those selected from the group consisting of lower alkyl having from 1–6 carbon atoms such as methyl, ethyl, propyl and the like, aralkyl such as benzyl, diphenylmethyl and the like. Substituted alkyl such as 2-aminoethyl, 3-aminopropyl, 2-formamidoylaminoethyl and the like and substituted aralkyl such as p-carboxybenzyl, p-aminobenzyl, p-hydroxybenzyl, pyridylmethyl, and the like; and

wherein R' is selected from the above-defined unsubstituted or substituted: alkyl, aralkyl, aryl for example:

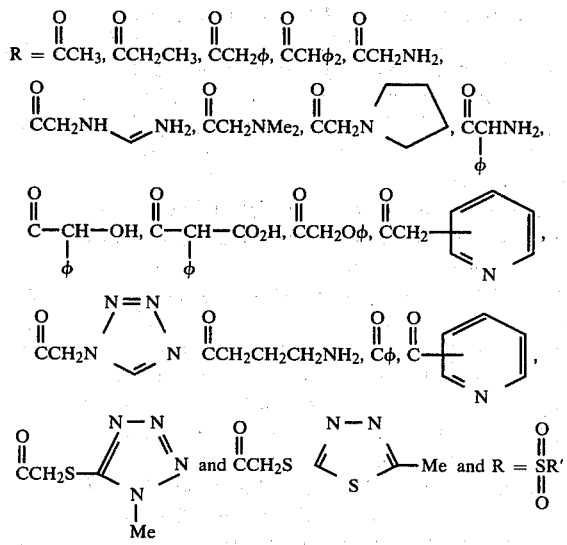

wherein R' is selected from the above-identified unsubstituted or substituted: alkyl or aryl, for example:

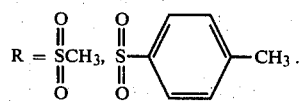

IDENTIFICATION OF THE RADICAL —COX'R³

As noted above, the compounds of the present invention may also generically be represented by the following structural formula:

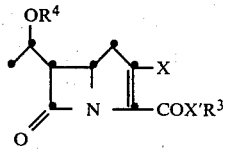

wherein X' is oxygen, sulfur or NR' (R' is hydrogen or loweralkyl having from 1 to 6 carbon atoms); and $R^3$ is hydrogen, or, inter alia, is representatively selected to provide the pharmaceutically acceptable salt, ester, anhydride ($R^3$ is acyl) and amide moieties known in the bicyclic β-lactam antibiotic art.

Suitable radicals ($R^3$) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups, wherein X'=O and $R^3$ is given:

(i) $R^3 = CR^a R^b R^c$ wherein at least one of $R^a$, $R^b$ and $R^c$ is an electron-donor, e.g., p-methoxyphenyl, 2,4,6-trimethylphenyl, 9-anthryl, methoxy, $CH_2SCH_3$, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^3 = CR^a R^b R^c$ wherein at least one of $R^a$, $R^b$ and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^3 = CR^a R^b R^c$ wherein at least two of $R^a$, $R^b$ and $R^c$ are hydrocarbon such as alkyl, e.g., methyl or ethyl, or aryl, e.g. phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^3 = R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

$R^4_3SiX'$; $R^4_2SiX'_2$; $R^4_3Si.NR^4_2$; $R^4_3Si.NH.COR^4$; $R^4_3Si.NH.CO.NH.SiR^4_3$; $R^4NH.CO.NH^4.SiR^4_3$; or $R^4C(OSiR^4_3)$; $HN(SiR^4_3)_2$ wherein X' is a halogen such as chloro or bromo and the various groups $R^4$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting I with alcohols, phenols, mercaptans, thiophenols, acylating reagents and the like. For example, esters and amides of interest are the above-listed starting materials and final products having the following group at the 2-position of Ia: —COX'R wherein X' is oxygen, sulfur, or NR' (R' is H or $R^3$), and $R^3$ is alkyl having 1-10 carbon atoms, straight or branched, such as methyl, ethyl, t-butyl, pentyl, decyl and the like; carbonylmethyl, including phenacyl, p-bromophenacyl, p-t-butylphenacyl, acetoxyacetylmethyl, pivaloxyacetylmethyl, carboxymethyl, and its alkyl and aryl esters, α-carboxy-αisopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1-10 and preferably 1-6 carbon atoms; but can be branched, straight or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-ylmethyl, and the like alkynyl having 1-10 carbon atoms, either straight or branched e.g., 3-pentenyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substitutents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2- thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1-4 carbon atoms chain); or phthalidyl; or phenylethyl, 2-(p-methylphenyl)-ethyl, and the arylthioalkyl analogues, aryloxyalkyl wherein aryl is preferably a phenyl ring having 0-3 substituents preferably 0 or 1 substituents in the ortho or para positions and alkyl is 1-6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4) benzyloxy)phenoxymethyl, (4-methyl)phenoxymethyl, (2-methoxy)phenoxymethyl, (1-phenoxy)ethyl, (4-amino)-phenoxymethyl, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X' is the

group. Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COX'R$^3$ are anhydrides wherein R$^3$ is acyl, for example, benzyloxycarbonyl, ethoxycarbonyl, benzoyl, and pivaloyl.

The most preferred —COX'R$^3$ radicals of the present invention are those wherein (relative to Structure IIa above X' is oxygen, sulphur or NR' (R' is selected from the group consisting of hydrogen and lower alkyl); and R$^{3'}$ is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

IDENTIFICATION OF R$^4$

In the generic representation of the present invention, structure I (above), the radical R$^4$ is, in addition to hydrogen, 1.) acyl (generically the group —OR$^4$ is classifiable as an ester); or 2.) R$^4$ is selected from alkyl, aryl, aralkyl, and the like such that the group —OR$^4$ is classifiable as an ether. For the ester embodiments (1) R$^4$ is selected from the following definition of acyl radicals (p=1). In the so-called ether embodiments (2.) of the present invention, R$^4$ is selected from the same acyl radicals wherein the carbonyl moiety,

or more generally

is deleted (p=0); thus R$^4$ is selected from the following radicals wherein all symbolism is defined below:

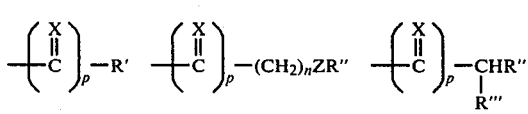

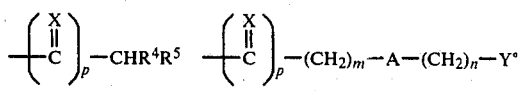

Thus, relative to the definition of R⁴, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R″ represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl), alkyl or alkoxy groups having 1 to about 6 carbon atoms, halo, such as Cl, Br, R and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R″ is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-amino-cyclohexyl, 2- and 3-thienylaminomethyl, 2-(5-nitrofuranyl)-vinyl, phenyl, o-methoxyphenyl, o-chlorophenyl, o-phenylphenyl, p-aminomethylbenzyl, 1-(5-cyanotriazolyl)-methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)-methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)-methyl, 3-furylmethyl, 2-thienylmethyl, 3-thienylmethyl, tetrazolylmethyl, benzamidinomethyl and cyclohexylamidinomethyl.

The acyl group can also be a radical of the formula:

wherein X is O or S and n is 0-4, Z represents oxygen, sulfur, carbonyl or nitrogen and R″ is defined as above. Representative members of the substituent

—(CH₂)ₙZR″ that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl-phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

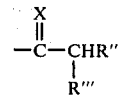

wherein R″ is defined as above and R‴ is a radical such as amino, hydroxy, azido, carbamoyl, guanidino, amidino, acyloxy, halo, such as Cl, F. Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(−)-α-hydroxybenzyl, α-carboxybenzyl, α-amino-(3-thienyl)methyl D(−)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl D(−)-2-thienyl-guanidinomethyl, D(−)-α-guanidinobenzyl α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono, and α-monoethylphosphono.

Further acyl radicals of interest in this class when X=oxygen are:

wherein $R^4$ and $R^5$ are as defined below. $R^4$ represents hydrogen, halo, such as chloro, fluoro, bromo, iodo, amino, guanidino, phosphono, hydroxy, tetrazolyl, carboxy, sulfo, or sulfamino and $R^5$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, siothiazolyl, tetrazolyl, oxadiazolyl, thiadiazolyl and and the like substituted heterocycles, phenylthio, phenyloxy lower alkyl of 1–6 carbon atoms, heterocyclic or substituted heterocyclic thio groups; or cyano. The substituents on the moieties, $R^4$ and $R^5$, can be halo, carboxymethyl, guanidino, guanidinomethyl, carboxamidomethyl, aminomethyl, nitro, methoxy or methyl. When $R^4$ is selected from the group consisting of hydrogen, hydroxy, amino or carboxy and $R^5$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorus (2) radicals:

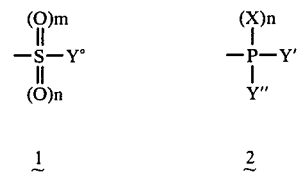

wherein with respect to 1, m and n are integers selected from 0 or 1 and $Y° = O^{\ominus}M^{\oplus}$, $-N(R'')_2$, and $R''$; wherein $M^{\oplus}$ is selected from hydrogen, alkali metal cations and organic bases; and $R''$ is as defined above, e.g., alkyl, alkenyl, aryl and heteroaryl. With respect to 2 X=O or S; n=0 or 1; and $Y'$ and $Y''$ are selected from the group consisting of $O^{\ominus}M^{\oplus}$, $-N(R'')_2$, $R''$ and $ZR''$ wherein all symbolism is as defined above, e.g., $R''$ and $ZR''$ are representatively: alkyl, alkenyl, aryl, heteroaryloxy, $Y'$ and $Y''$, including $R''$ moieties, can be joined together to form cyclic ester, ester-amide and amide functions.

An acyl class of particular interest is those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as trilower alkylsilyl, for examples, trimethylsilyl and t-butyldimethyl are also of interest.

The following radicals, according to the foregoing definition of acyl, are especially preferred for $R^4$ of structure Ia: formyl, acetyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylamino-acetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanidinoacetyl, 3-guanidinopropionyl, $N^3$-methylguanidinopionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl, sulfo, phosphono,

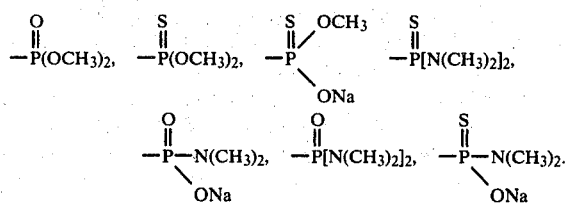

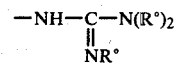

wherein R° is as defined in (2) (above).

(4) guanyl and substituted guanyl

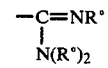

wherein R° is as defined in (2) (above).

(5) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is H or loweralkyl having 1-6 carbon atoms):

Another class of acyl radicals are terminally substituted acyls wherein the substituent is a basic group such as substituted and unsubstituted: amino, amidino, guanidino, guanyl and nitrogen-containing mono- and bicyclic heterocyles (aromatic and non-aromatic) wherein the hetero atom or atoms, in addition to nitrogen, are selected from oxygen and sulphur. Such substituted acyls may be represented by the following formula:

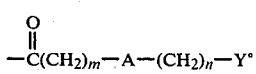

wherein m, and n are integers selected from 0 to 5; A is O, NR' (R' is hydrogen or loweralkyl having 1-6 carbon atoms), S or A represents a single bond; and Y° is selected from the following group:

(1) amino or substituted amino

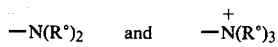

wherein the values for R° are independently selected from: hydrogen; N(R')$_2$ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms, two R° groups may be joined together with the N atom to which they are attached to form a ring having 3-6 atoms.

(2) amidino and substituted amidino

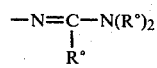

wherein the value of R° is independently selected from the group consisting of: hydrogen; N(R')$_2$ (R' is hydrogen or loweralkyl having 1-6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

(3) guanidino and substituted guanidino

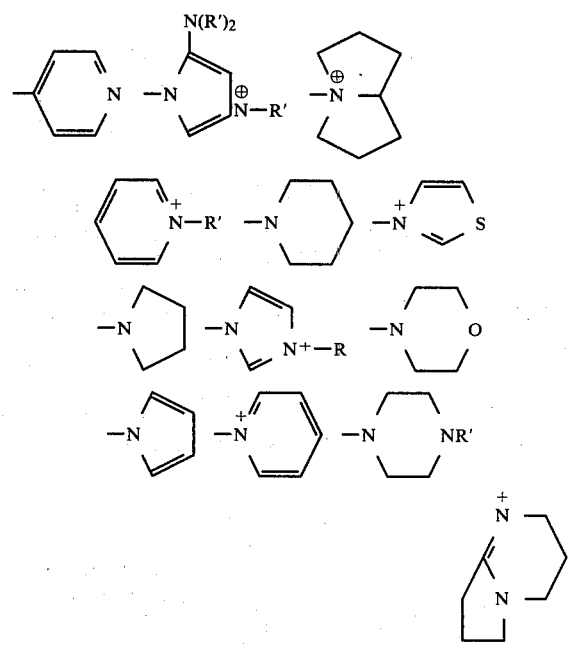

The following specific acyl radicals falling within this class are additionally representative:

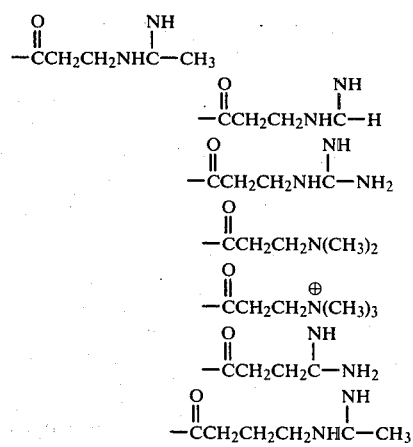

-continued

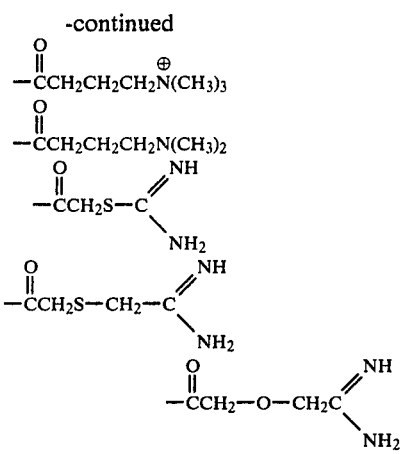

Relative to the generic expression of the compounds of the present invention (Ia):

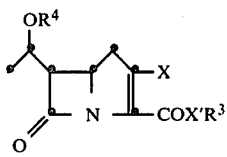

The radicals $R^4$ and/or $X'R^3$ may be established after synthesis, rather than being established during the course of synthesis, by operating upon the hydroxyl group and/or the carboxyl group. Ester embodiments (carboxyl derivatives) are conveniently prepared by conventional procedures known in the art. Such procedures include:

(1) Reaction of I with a diazoalkane such as diazomethane, phenyldiazomethane, diphenyldiazomethane and the like in an inert solvent such as dioxane, THF, halohydrocarbons, acetonitrile, ethylacetate, and the like at a temperature of from −78° C. to 25° C. for from a few minutes to 2 hours.

(2) Reaction of the metallic salts (e.g., Na, Li) of the acid (I) with an activated alkyl halide such as methyliodide, benzylbromide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, THF, dioxane, and the like at a temperature of from −78° C. to 25° C. for from a few minutes to 4 hours.

(3) Reaction of the free acid (I) with an alcohol such as methanol, ethanol, benzyl alcohol, and the like. This reaction may be conducted in the presence of a carbodiimide condensing agent such as dicyclohexylcarbodiimide or the like. Suitable solvents, at a temperature of from 0° C. to reflux for from 15 minutes to 18 hours, include $CHCl_3$, $CH_3CH$, $CH_2Cl_2$ and the like.

(4) Reaction of an acid anhydride of I, prepared by reacting the free acid (I) with an acid chloride such as ethylchloroformate, benzychloroformate and the like, with an alcohol such as those listed in (3) under the same conditions of reaction as given above for (3). The anhydride is prepared by reaction I and the acid chloride in a solvent such as tetrahydrofuran (THF), $CH_2Cl_2$ and the like at a temperature of from 25° C. to reflux for from 15 minutes to 10 hours.

(5) Reaction of labile esters of I such as the trimethylsilyl ester, dimethyl-t-butylsilyl ester or the like with RX' wherein X' is halogen such as bromo and chloro and R is as defined in a solvent such as THF, $CH_2Cl_2$ and the like at a temperature of from 0° C. to reflux for from 15 minutes to 16 hours.

The amides of the present invention are most conveniently prepared by reacting the acid anhydride of I with ammonia or with the amine of choice, e.g., the alkyl-, dialkyl-, aralkyl- or heterocyclic amines listed above.

The above-recited schemes of esterification are well-known in the related bicyclic β-lactam antibiotic art and indeed in all of general organic synthesis as and it is to be noted that there is no undue criticality of reaction parameters in the preparation of the compounds of the present invention.

In general, the compounds of the present invention are prepared by any of a variety of well-known esterification or etherification reactions upon the secondary alcoholic group of I in its protected carboxyl form, II. Such procedures (II→III) include:

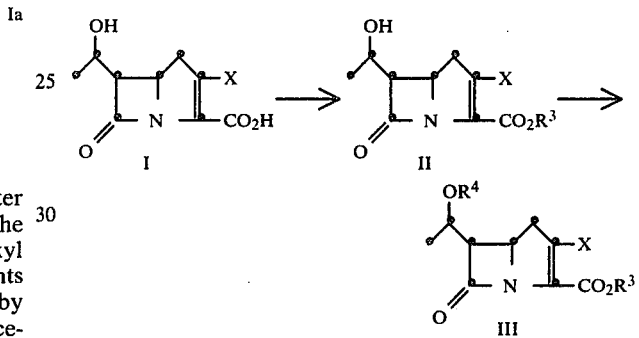

(1) For the preparation of ether ($OR^4$) embodiments of the present invention, the acid catalized reaction II with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from −78° C. to 25° C. for from a few minutes to 2 hours.

(2) For the preparation of ether ($OR^4$) embodiments of the present invention, the reaction of II with an alkylating agent such as active halides, for example, methyliodide, benzylbromide, m-phenoxybenzylbromide, and the like, alkyl sulphonates such as dimethylsulfate, diethylsulphate, methylfluorosulfonate, and the like in the presence of a strong base capable of forming the alcoholate anion of III. Suitable bases include alkali and alkaline earth metal oxides and hydrous oxides, alkali metal alkoxides such as potassium tertiary-butoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from −78° C. to 25° C., for from a few minutes to 4 hours.

(3) For the preparation of ester ($OR^4$) embodiments, of the present invention, the reaction of II with any of the above-listed acyl radicals in their acid form. This reaction may be conducted in the presence of a carbodiimide condensing agent such as dicyclohexylcarbodiimide or the like. Suitable solvents include any inert solvent such as $CHCl_3$, $CH_2Cl_2$ DMF, HMPA, acetone, dioxane and the like at a temperature of from 0° C. to 60° C. for from 15 minutes to 12 hours.

(4) For the preparation of ester ($OR^4$) embodiments of the present invention, the reaction of II with an acyl halide or an acid anhydride, wherein the acyl moiety is described above. Generally, when the above-described acylating reaction employs an acid halide (suitable halides are chloro, iodo or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylene, pyridine, and the like at a temperature of from 0° C. to 40° C. for from 1 to 4 hours.

Suitable acyl halides and anhydrides include: acetic anhydride, bromoacetic anhydride, propionic anhydride, benzoylchloride, phenylacetyl chloride, azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl ethyl, 2-furoyl ethyl carbonic anhydride, methylchloroformate, bis(p-nitrobenzyl)phosphorochloridate and the like.

(5) For the preparation of ester ($OR^4$) embodiments of the present invention, the reaction of II with a suitably substituted ketene or isocyanate such as ketene, dimethyl ketene, methylisocyanate, methylisothiocyanate, chlorosulfonyl isocyanate and the like. Suitable solvents include dioxane, tetrohydrofuran, chloroform and the like at a temperature of from −70° C. to 60° C. for from 15 minutes to 18 hours.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative of such salts are sodium, potassium, and calcium salts and amine salts such as benzhydrylamino, N-benzyl-2-phenethylamino, N,N'-dibenzylethylenediamine and procaine salts.

The salts of this invention are pharmacologically acceptable non-toxic derivatives which can be used as the activeingredient in suitable unit dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae,* Serratia, *Salmonella typhosa,* Pseudomonas and *Bacterium proteus.* The antibacterials of the invention may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, or polyvinylpyrrolidone; fillters for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose contains with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 100 mg. to 1000 mg. In parenteral administration the unit dosage is usually the pure compound in a slightly acidified sterile water solution or in the form of a soluble powder intended for solution.

The following Examples, illustrate but do not limit the product, process, compositional or method of treatment aspects of the present invention. All temperatures are expressed in °C.

EXAMPLE 1

Preparation of 4-(2-Acetoxyethyl)-azetidin-2-one

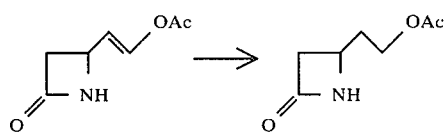

A mixture of 4-(2-acetoxyvinyl)-azetidin-2-one (3.00 g), 10% Pd/C (0.15 g) and ethylacetate (EtOAc) (120 ml) is hydrogenated in a 500 ml glass bomb on a Parr shaker at an initial pressure of 39 psi. After shaking 10 mins (final pressure of 20 psi), the mixture is filtered through a pad of MgSO$_4$ to remove the catalyst. The filtrate is concentrated in vacuo and the residue stripped with anhydrous benzene to provide 4-(2-acetoxyethyl)-azetidin-2-one (3.098 g) as a clear oil: ir(neat) 3.01, 5.66, 5.75, 7.28, 8.05, and 9.61 cm$^{-1}$; nmr (CDCl$_3$) δ1.95 (m, 2), 2.07 (s, 3), 2.60 (m, 1), 3.12 (m, 1), 3.70 (m, 1), 4.15 (m, 2), and 6.77 (br s, 1).

EXAMPLE 2

Preparation of N-(t-Butyldimethylsilyl)-4-(2-acetoxyethyl)-azetidin-2-one

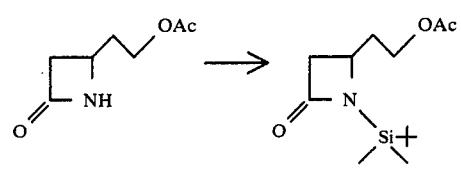

Triethylamine (Et$_3$N) (2.96 ml, 21.2 mmol) and t-butyldimethylsilyl chloride (3.059 g, 20.3 mmol) are added to an ice-cold stirring solution of 4-(2-acetoxyethyl)-azetidin-2-one (3.098 g, 19.3 mmol) in anhydrous dimethylformamide (DMF) (20 ml). A white precipitate appears immediately. The cooling bath is removed and the mixture is stirred at 25° C. (room temperature) for 5 mins. The mixture is diluted with benzene (200 ml), washed with H$_2$O (5×80 ml) and brine, dried with MgSO$_4$, filtered, and evaporated under reduced pressure to afford N-(t-butyldimethylsilyl)-4-(2-acetoxyethyl)-azetidin-2-one (5.078 g) as an off white solid: ir(neat) 5.75, 8.08, 8.41, 11.92, and 12.18 cm$^{-1}$; nmr (CDCl$_3$) δ0.25 (s, 6), 0.98 (s, 9), 1.97 (m, 2), 2.05 (s, 3), 2.67 (dd, 1), 3.20 (dd, 1) 3.62 (m, 1), and 4.12 (t, 2); mass spectrum m/e 214 (M$^+$ −57) and 172.

EXAMPLE 3

Preparation of N-(t-Butyldimethylsilyl)-4-(2-hydroxyethyl)-azetidin-2-one

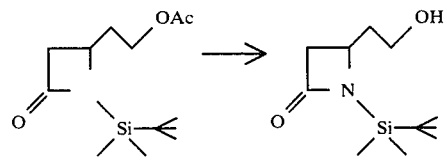

A solution of N-(t-butyldimethylsilyl)-4-(2-acetoxyethyl)-azetidin-2-one (41.7 g, 0.154 mmol) in anhydrous methanol (415 ml) is stirred under a N$_2$ atmosphere with ice-bath cooling. A solution of sodium methoxide (415 mg, 7.7 mmol) in anhydrous methanol (15 ml) is added and the resulting solution is stirred in the cold for 2 more hrs. Acetic acid (2.2 ml) is then added and the solvents are evaporated in vacuo (i.v.). The residue is taken up in EtOAc (300 ml), washed with H$_2$O (4×75 ml), 5% NaHCO$_3$ (75 ml) and brine, dried with MgSO$_4$ and evaporated i.v. to a clear oil (21.3 g). This material is purified by chromatography on a Baker silica gel column (425 g, packed under EtOAc). After a 100 ml forefraction, 25 ml EtOAc fractions are collected every 2.5 mins. Fractions 41–49 yield starting material and fractions 51–90 afford N-(t-butyldimethylsilyl)-4-(2hydroxyethyl)-azetidin-2-one (19.4 g) as a clear oil: ir (neat) 2.88, 5.73, 5.80, 7.52, 7.67, 7.99, 8.40, 11.95, and 12.18 cm$^{-1}$; nmr (CDCl$_3$) δ0.25 (s, 6), 0.98 (s, 9), 1.82 (m, 2), 2.67 (dd, 1), 3.17 (dd, 1), 3.67 (t, 2), and 3.67 (m, 1); mass spectrum m/e 172.

EXAMPLE 4

Preparation of
N-(t-Butyldimethylsilyl)-4-(2-oxoethyl)-azetidin-2-one

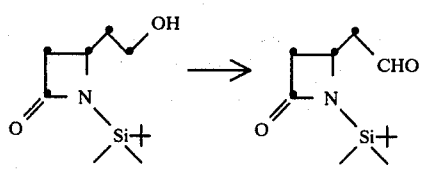

Anhydrous chromium trioxide (CrO₃) (1.94 g, 19.4 mmol) is added to a solution of anhydrous pyridine (3.07 g, 38.8 mmole) in anhydrous methylene chloride (CH₂Cl₂) (50 ml). The resulting mixture is stirred at room temperature for 15 mins. A solution of N-(t-butyldimethylsilyl)-4-(2-hydroxyethyl)-azetidin-2-one (0.74 g, 3.23 mmol) in anhydrous CH₂Cl₂ (5 ml) is added all at once. After stirring at room temperature for 5 mins, the mixture is decanted and the dark, gummy residue is washed with more CH₂Cl₂. The combined CH₂Cl₂ supernatant is evaporated i.v. The residue is taken up in diethyl ether and filtered to remove chromium salts. The ethereal filtrate is washed with 5% NaHCO₃, 5% HCl, 5% NaHCO₃ and brine, dried with MgSO₄, filtered, and evaporated i.v. to yield N-(t-butyldimethylsilyl)-4-(2-oxoethyl)-azetidin-2-one (0.54 g) as an off-white solid: ir(CHCl₃) 5.77, 5.80, 7.36, 7.60, 7.99, 8.50 and 11.95 cm⁻¹; nmr (CDCl₃) δ0.23 (s, 3), 0.27 (s, 3), 0.98 (s, 9), 2.63 (ddd, 1), 2.65 (dd, 1), 3.07 (ddd, 1), 3.37 (dd), 3.97 (m, 1), and 9.78 (t, 1); mass spectrum m/e 170 and 128.

EXAMPLE 5

Preparation of
N-(t-Butyldimethylsilyl)-4-(3-benzyloxycarbonyl-2-hydroxypropyl)-azetidin-2-one

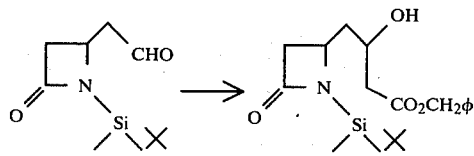

To a flame dried, 50 ml, 3-neck flask fitted with a N₂ inlet, magnetic stirrer, addition funnel, and serum cap are added anhydrous tetrahydrofuran (THF) (10.5 ml) and diisopropyl amine (0.579 ml, 4.13 mmol). The solution is cooled in an ice-methanol bath under N₂ and treated with 2.4 N n-butyl lithium in hexane (1.72 ml). After being stirred at −10° for 15 mins, the solution is cooled to −78° and treated dropwise over 9 mins with a solution of benzyl acetate (0.620 g, 4.13 mmol) in anhydrous THF (3.5 ml). After stirring 15 more mins at −78° C., the reaction mixture is treated dropwise over 13 mins with a solution of N-(t-butyldimethylsilyl)-4-(2-oxoethyl)-azetidin-2-one (0.894 g, 3.93 mmol) in anhydrous THF (6 ml). The reaction mixture is stirred at −78° an additional 15 mins and then quenched with 2.5 N HCl (6 ml). EtOAc (100 ml) is added and the organic phase is separated, washed with H₂O (2×20 ml), 5% NaHCO₃ (20 ml) and brine, dried with MgSO₄, and filtered. The filtrate is evaporated i.v. and the residue stripped with φH to yield N-(t-butyldimethylsilyl)-4-(3-benzyloxycarbonyl-2-hydroxypropyl)-azetidin-2-one (1.432 g) as an oil; ir (neat) 2.87, 5.73, 5.79, 7.57, 7.96, 8.39, 11.92, and 12.16 cm⁻¹; mass spectrum m/e 362, 320, 278, 170 and 128.

EXAMPLE 6

Preparation of
N-(t-Butyldimethylsilyl)-4-(3-benzyloxycarbonyl-2-oxopropyl)-azetidin-2-one

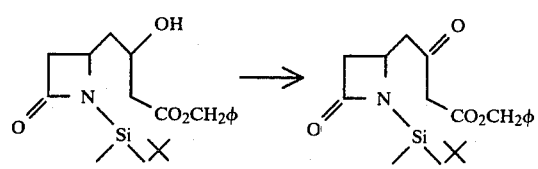

Anhydrous CrO₃ (2.274 g, 22.74 mmol) is added to a solution of anhydrous pyridine (3.597 g, 45.48 mmol) in anhydrous CH₂Cl₂ (60 ml). After stirring at room temperature for 15 mins, the reaction mixture is treated all at once with a solution of N-(t-butyldimethylsilyl)-4-(3-benzyloxycarbonyl-2-hydroxypropyl)-azetidin-2-one (1.432 g, 3.79 mmol) in anhydrous CH₂Cl₂ (25 ml). The resulting mixture is stirred at 25°· C. for 5 mins. The CH₂Cl₂ layer is decanted from the dark, gummy residue which is triturated with more CH₂Cl₂. The combined CH₂Cl₂ phase is evaporated i.v. The residue is triturated with diethylether (Et₂O) (100 ml) in several portions and the Et₂O extracts are filtered to remove chromium salts. The ethereal filtrate is washed with 5% NaHCO₃, 1 N HCl, 5% NaHCO₃ and brine, dried with MgSO₄, filtered, and evaporated i.v. to yield N-(t-butyldimethylsilyl)-4-(3-benzyloxycarbonyl-2-oxopropyl)-azetidin-2-one (1.042 g) as a pale yellow oil: ir (neat) 5.72 (3 poorly resolved peaks), 7.59 7.98, 8.42, and 11.93 cm⁻¹; nmr (CDCl₃) δ0.18 (s, 3), 0.22 (s, 3), 0.97 (s, 9), 2.53 (dd, 1), 2.63 (dd, 1), 3.13 (dd, 1), 3.28 (dd, 1), 3.47 (s, 2), 3.88 (m, 1), 5.17 (s, 2), and 7.33 (s, 5); mass spectrum m/e 360, 318, and 2.76.

EXAMPLE 7

Preparation of
4-(3-Benzyloxycarbonyl-2-oxopropyl)-azetidin-2-one

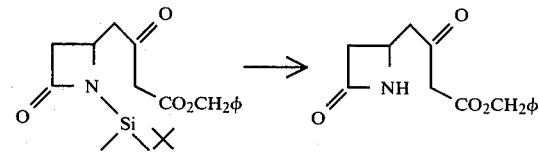

N-(t-butyldimethylsilyl)-4-(3-benzyloxycarbonyl-2-oxopropyl)-azetidin-2-one (302 mg, 0.80 mmol) is dissolved in acetic acid (4.0 ml) and the solution is diluted with H₂O (2.0 ml). The resulting solution is stirred in a securely stoppered, 10 ml, round-bottom flask in an oil bath maintained at 73° C. for 7 hrs. After cooling to room temperature, the reaction mixture is diluted with EtOAc and toluene and evaporated i.v. The residue is stripped twice with toluene to yield a yellow oil (220 mg). The crude product is chromatographed on Baker silica gel (8.8 g, packed under EtOAc). The column is eluted with EtOAc; 3 ml fractions being collected every 2.25 mins. Fractions 14–30 are combined and evaporated i.v. to provide 4-(3-benzyloxycarbonyl-2-oxopropyl)-azetidin-2-one (114 mg) as a clear oil; ir (neat) 3.04, 5.68, 5.72 and 5.83 cm$^{-1}$; nmr (CDCl$_3$) δ2.52 (ddd, 1), 2.67 (dd, 1), 3.02 (dd, 1), 3.12 (ddd, 1), 3.48 (s, 2), 3.88 (m, 1), 5.18 (s, 2), 6.17 (m, 1), and 7.37 (s, 5); mass spectrum m/e 261 (M+), 233, 219, 192, 127 and 91.

EXAMPLE 8

Preparation of 4-(3-Benzyloxycarbonyl-3-diazo-2-oxopropyl)-azetidin-2-one

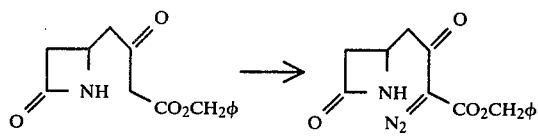

Freshly recrystallized p-carboxy benzene sulfonylazide (241 mg, 1.06 mmol) is added to a solution of 4-(3-benzyloxycarbonyl-2-oxopropyl)-azetidin-2-one (276 mg, 1.06 mmol) in anhydrous acetonitrile (6.6 ml). The resulting suspension is cooled in an ice-bath and stirred while Et$_3$N (443 μl, 3.18 mmol) is added. The resulting yellow solution is stirred at room temperature. A precipitate forms quickly. After 90 mins, the mixture is diluted with EtOAc (50 ml) and filtered. The filtrate is washed with H$_2$O (2×10 ml), 0.5 N NaOH (2×10 ml), H$_2$O (4×10 ml) and brine, dried with MgSO$_4$, filtered, and evaporated i.v. to an off-white solid (273 mg). This is triturated with Et$_2$O to provide 4-(3-benzyloxycarbonyl-3-diazo-2-oxopropyl)-azetidin-2-one (227 mg) as a cream colored powder: ir (film from CHCl$_3$) 3.0, 4.65, 5.66, 5.82, 6.05, 7.21, 7.70 and 8.23 cm$^{-1}$; nmr (CDCl$_3$) δ2.63 (ddd, 1), 2.97 (dd, 1), 3.15 (ddd, 1), 3.40 (dd, 1), 3.98 (m, 1), 5.27 (s, 2), 6.13 (m, 1), and 7.38 (s, 5); mass spectrum m/e 259, 245, 231, and 218.

EXAMPLE 9

Preparation of Benzyl 1-azabicyclo[3.2.0]heptan-3,7-dione-2-carboxylate

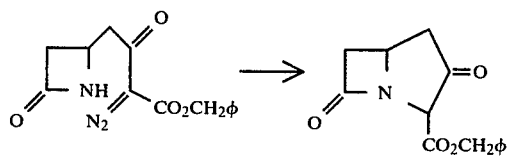

A solution of 4-(3-benzyloxycarbonyl-3-diazo-2-oxopropyl)-azetidin-2-one (20 mg) in anhydrous benzene (5 ml) is irradiated for 60 mins at room temperature using a Hanovia 450 W medium-pressure mercury lamp and a Pyrex filter. Dry N$_2$ is bubbled through the solution prior to and during the photolysis. Evaporation of the solvent in vacuo gives an oil (17 mg) which is purified by chromatography on a 250μ×20×20 cm silica gel GF plate using 3:1 φH-EtOAc as developing solvent. The band at Rf 0.3 is removed and eluted with EtOAc to give a clear oil (2.4 mg). This material is further purified by tlc on a 250μ×7.5×8.5 cm silica gel GF plate. The cleanly resolved band at Rf 0.29 is removed and eluted with EtOAc to give benzyl 1-azabicyclo[3.2.0]heptan-3,7-dione-2-carboxylate (0.7 mg) as a clear oil: ir (CCl$_4$) 1783, 1773, and 1744 cm$^{-1}$; ir (CHCl$_3$) 1767, 1741 cm$^{-1}$; uv (Cy) 215 nm; nmr (CDCl$_3$) δ2.36 (dd, J=8 and 18.5, 1), 2.90 Cdd, J=6 and 18.5, 1), 2.92 (dd, J=2 and 16, 1), 3.63 (dd, J=5 and 16, 1), 4.11 (m, 1), 4.71 (s, 1), 5.19 (s, 2) and 7.33 (s, 5); mass spectrum m/e 259 (M+), 231 (M+ −28), 217 (M+ −42) 203, 187, 186, 168 (M+ −91), 124, and 91; high resolution mass spectrum m/e 259.0842 (C$_{14}$H$_{13}$NO$_4$).

EXAMPLE 10

Preparation of Benzyl 3-chloro-1-azabicyclo[3.2.0]hept-2-en-7-one-2-carboxylate

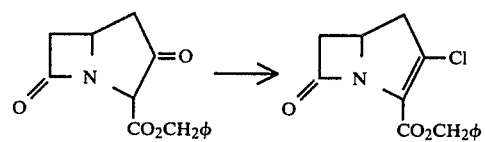

Benzyl 1-azabicyclo[3.2.0]heptane-3,7-dione-2-carboxylate (26 mg, 0.1 mmol) in anhydrous DMF (0.5 ml) containing PCl$_3$ (27 mg, 0.2 mmol) is kept at 25° C. for 5 hrs. The mixture is diluted with toluene (5 ml), washed with H$_2$O (5×1 ml), 5% HCl (2 ml), 5% NaHCO$_3$ (2 ml) and brine, dried with MgSO$_4$, and filtered. Evaporation of the solvent in vacuo provides crude benzyl 3-chloro-1-azabicyclo[3.2.0]hept-2-en-7-one-2-carboxylate.

EXAMPLE 11

Preparation of Benzyl 3-bromo-1-azabicyclo[3.2.0]hept-2-en-7-one-2-carboxylate

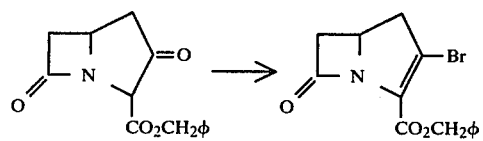

By substituting PBr$_3$ (54 mg) for PCl$_3$ in the preceeding example, benzyl 3-bromo-1-azabicyclo[3.2.0]hept-2-en-7-one-2-carboxylate is obtained.

EXAMPLE 12

Preparation of Benzyl 3-acetoxy-1-azabicyclo[3.2.0]hept-2-en-7-one-2-carboxylate

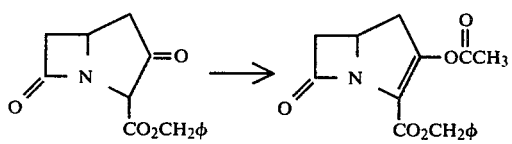

Method A

A solution of benzyl 1-azabicyclo[3.2.0]heptan-3,7-dione-2-carboxylate (13 mg, 0.05 mmol) in anhydrous CH$_2$Cl$_2$ (1 ml) is cooled in an ice-bath and treated with triethylamine (Et$_3$N) (7 μl, 0.05 mmol). Ketene is passed through the resulting solution for 10 mins. The solvent and excess ketene are removed in vacuo to leave crude benzyl 3-acetoxy-1-azabicyclo[3.2.0]hept-2-en-7-one-2-carboxylate.

Method B

A solution of benzyl 1-azabicyclo[3.2.0]heptan-3,7-dione-2-carboxylate (20 mg) in anhydrous pyridine (200 μl) and Ac₂O (100 μl) is kept at 0° C. for 8 hrs. The mixture is evaporated in vacuo and the residue dissolved in EtOAc. This solution is washed with pH 2 phosphate buffer, 5% NaHCO₃, and brine, dried with MgSO₄, filtered, and evaporated i.v. to provide benzyl 3-acetoxy-1-azabicyclo[3.2.0]hept-2-en-7-one-2-carboxylate. By substituting Ac₂O with

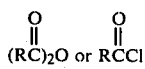

in Method B, various 3-acyloxy derivatives are obtained.

EXAMPLE 13

Preparation of Benzyl 3-(α-azidoacetoxy)-1-azabicyclo[3.2.0]hept-2-en-7-one-2-carboxylate

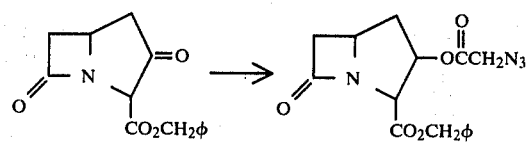

Azidoacetyl chloride (21 μl) is added by syringe in an ice-cold, stirring solution of triethylamine (42 μl) and benzyl 1-azabicyclo[3.2.0]heptane-3,7-dione-2-carboxylate (52 mg) in anhydrous methylene chloride (2 ml). After stirring 30 mins in the cold, the reaction mixture is diluted with methylene chloride (5 ml), washed with H₂O (2 ml), pH 3 phosphate buffer (2 ml), and 5% NaHCO₃ (2 ml), dried with MgSO₄, filtered, and evaporated in vacuo. Chromatography of the residue on a silica gel GF plate gives benzyl 3-(α-azidoacetoxy)-1-azabicyclo[3.2.0]hept-2-en-7-one-2-carboxylate.

EXAMPLE 14

Preparation of Benzyl 3-toluenesulfonyloxy-1-azabicyclo[3.2.0]hept-2-en-7-one-2-carboxylate

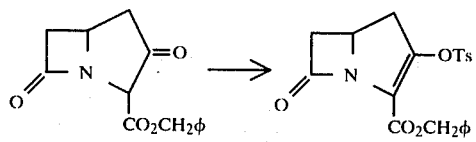

p-Toluenesulfonic anhydride (33 mg, 0.1 mmol) and Et₃N (17 μl, 0.12 mmol) are added to a solution of benzyl 1-azabicyclo[3.2.0]heptan-3,7-dione-2-carboxylate (26 mg., 0.1 mmol) in anhydrous CH₂Cl₂ (2 ml). The resulting solution is stirred at room temperature for 2 hours. The mixture is diluted with CH₂Cl₂ (10 ml), washed with H₂O (2×5 ml), pH 3 phosphate buffer (5 ml) and 5% NaHCO₃ (5 ml), dried with MgSO₄, filtered and evaporated i.v. to provide benzyl 3-toluenesulfonyloxy-1-azabicyclo[3.2.0]hept-2-en-7-one-2-carboxylate.

EXAMPLE 15

Preparation of Benzyl 3-methoxy-1-azabicyclo[3.2.0]hept-2-en-7-one-2-carboxylate

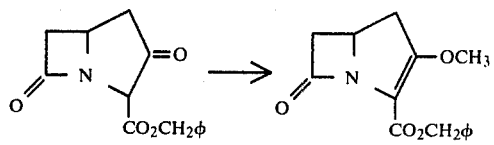

A solution of benzyl 1-azabicyclo[3.2.0]heptan-3,7-dione-2-carboxylate (26 mg) in anhydrous methanol (1 ml) at 0° C. is treated with ethereal CH₂N₂ until a yellow color persists. The mixture is stirred 15 more minutes in the cold and then evaporated in vacuo. Chromatography of the residue on silica gel provides benzyl 3-methoxy-1-azabicyclo[3.2.0]hept-2-en-7-one-2-carboxylate.

EXAMPLE 16

Preparation of Benzyl 3-(2-azidoethyloxy)-1-azabicyclo[3.2.0]hept-2-en-7-one-2-carboxylate

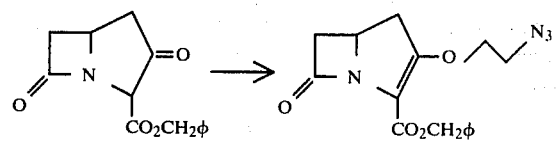

A mixture of benzyl 1-azabicyclo[3.2.0]heptane-3,7-dione-2-carboxylate (26 mg) and 2-azidoethyl trifluoromethyl sulfonate (26 mg) in anhydrous acetene (0.5 ml) containing powdered potassium carbonate (28 mg) is stirred at 25° C. in a capped flask for 2 hrs. The mixture is diluted with anhydrous ether (5 ml) and filtered. The filtrate is washed with water (2 ml) and brine, dried with MgSO₄, filtered, and evaporated in vacuo. The residue is purified by plc on a silica gel GF plate to afford benzyl 3-(2-azidoethyloxy)-1-azabicyclo[3.2.0-]hept-2-en-7-one-2-carboxylate.

EXAMPLE 17

Preparation of Benzyl 6-(1-hydroxyethyl)-1-azabicyclo[3.2.0]heptane-3,7-dione-2-carboxylate

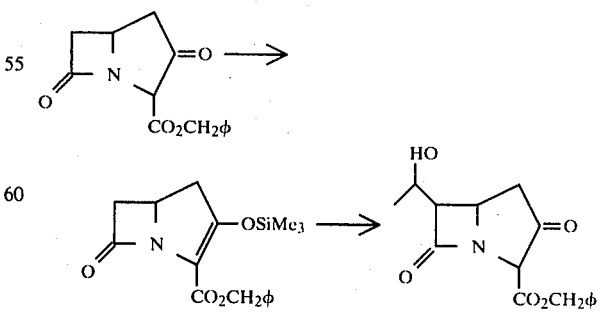

A solution of benzyl 1-azabicyclo[3.2.0]heptane-3,7-dione-2-carboxylate (130 mg, 0.5 mmol) in anhyd. Et₂O (4 ml) containing Et₃N (61 mg, 0.6 mmol) is stirred under a N₂ atmosphere with ice-bath cooling. A solution of Me₃SiCl (60 mg, 0.55 mmol) in anhyd. Et₂O (1 ml) is added dropwise and the resulting mixture is stirred in the cold for 2 hrs. The mixture is filtered under a N₂ atmosphere and the precipitate is washed with more anhydrous Et₂O. The combined filtrate and washings is evaporated in vacuo to provide benzyl 3-trimethylsilyloxy-1-azabicyclo[3.2.0]hept-2-en-3-one-2-carboxylate. This material is dissolved in anhydrous THF (0.5 ml) and used immediately in the next step.

The trimethylsilyloxy derivative in THF is added all at once to a solution of lithium diisopropylamide (0.55 mmol) in THF at −78° (prepared by adding 0.34 ml of 1.6 N n-BuLi in hexane to 56 mg of diisopropylamine in 2.5 ml of anhyd. THF and stirring for 15 mins at 0°). The reaction mixture is stirred at −78° and under a N₂ atm for 5 mins. Freshly distilled acetaldehyde (66 mg, 1.5 mmol) is then added all at once and the reaction mixture is stirred at −78° for 10 sec. Saturated aqueous NH₄Cl solution (3 ml) is added and the resulting mixture is allowed to warm to 0° with vigorous stirring. The mixture is extracted with EtOAc (3×5 ml) and the combined extracts are washed with brine, dried over MgSO₄, filtered, and evaporated i.v. Chromatography of the residue on silica gel affords the diastereomeric benzyl 6-(1-hydroxyethyl)-1-azabicyclo[3.2.0]heptane-3,7-dione-2-carboxylates.

Following the above procedure except substituting other 3-substituted derivatives the following representative species of the present invention are obtained.

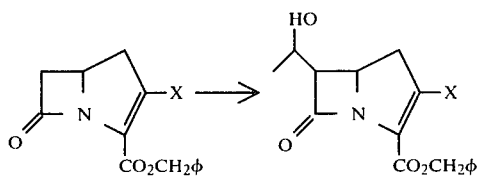

wherein X is methoxyl, toluenesulfonyloxy, chloro and bromo, respectively.

EXAMPLE 18

Preparation of Sodium 6-(1-hydroxyethyl)-1-azabicyclo[3.2.0]heptane-3,7-dione-2-carboxylate

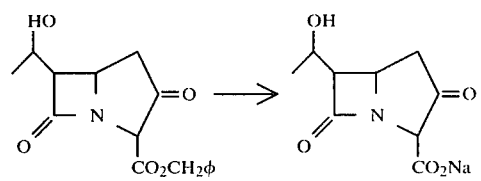

Benzyl 6-(1-hydroxyethyl)-1-azabicyclo[3.2.0]heptane-3,7-dione-2-carboxylate (30 mg) is dissolved in dioxane (2 ml). The solution is treated with ethanol (0.5 ml), H₂O (0.5 ml), NaHCO₃ (8.5 mg) and 10% Pd/C (20 mg) and the resulting mixture is hydrogenated at 40 psi for 1 hr. The mixture is filtered to remove the catalyst which is washed with H₂O (2.5 ml). The combined filtrate is extracted with ethyl acetate (3×2 ml), concentrated in vacuo, and lyophilized to provide sodium 6-(1-hydroxyethyl)-1-azabicyclo[3.2.0]heptane-3,7-dione-2-carboxylate.

EXAMPLE 19

Preparation of Benzyl 6-(1-hydroxyethyl)-3-toluenesulfonyloxy-1-azabicyclo[3.2.0]hept-2-en-7-one-2-carboxylate

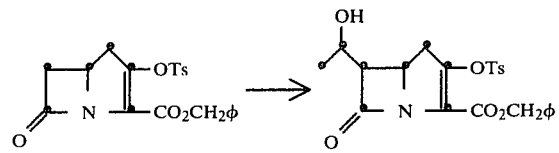

A solution of benzyl 3-toluenesulfonyloxy-1-azabicyclo[3.2.0]hept-2-en-7-one-2-carboxylate (41 mg) in anhydrous THF (0.5 ml) is added dropwise over 5 mins to a stirring solution of lithium diisopropylamide (from 15.5 μl of diisopropylamine and 0.07 ml of 1.6 N BuLi) in anhydrous THF (1.5 ml) at −78°. The resulting solution is stirred at −78° for 10 mins and then treated with acetaldehyde (56 μl). After 5 more mins, saturated aqueous NH₄Cl solution (1.5 ml) is added and the mixture is allowed to warm to room temperature. The mixture is diluted with ethyl acetate (20 ml), washed with H₂O and brine, dried with MgSO₄, filtered, and evaporated in vacuo to provide benzyl 6-(1-hydroxyethyl)-3-toluenesulfonyloxy-1-azabicyclo[3.2.0]-hept-2-en-7-one-2-carboxylate as a mixture of diastereomers.

EXAMPLE 20

Preparation of Sodium 6-(1-hydroxyethyl)-3-toluenesulfonyloxy-1-azabicyclo[3.2.0]hept-2-en-7-one-2-carboxylate

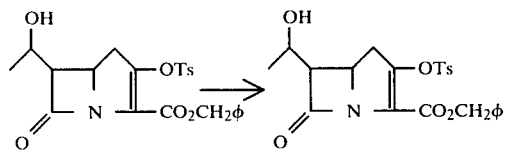

A mixture of benzyl 6-(1-hydroxyethyl)-3-toluenesulfonyloxy-1-azabicyclo[3.2.0]hept-2-en-7-one-2-carboxylate (30 mg), 10% palladium on charcoal (30 mg), sodium bicarbonate (6 mg), dioxane (3 ml) and water (1 ml) is hydrogenated at 40 psi for 30 mins. The mixture is filtered to remove the catalyst which is washed with water (3×3 ml) The combined filtrate is extracted with ethylacetate (3×2 ml), concentrated in vacuo to ca. 2 ml, and lyophilized to give sodium 6-(1-hydroxyethyl)-3-toluenesulfonyloxy-1-azabicyclo[3.2.0]hept-2-en-7-one-2-carboxylate.

EXAMPLE 21

Preparation of Benzyl 6-(1-hydroxyethyl)-3-(2-azidoethyloxy)-1-azabicyclo[3.2.0]hept-2-en-7-one-2-carboxylate

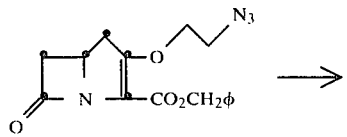

-continued

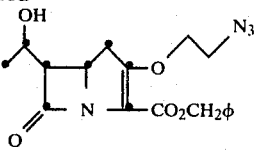

Benzyl 3-(2-azidoethyloxy)-1-azabicyclo[3.2.0]hept-2-en-7-one-2-carboxylate is reacted with lithium diisopropylamide and acetaldehyde as described in Example 19 to provide benzyl 6-(1-hydroxyethyl)-3-(2-azidoethyloxy)-1-azabicyclo[3.2.0]hept-2-en-7-one-2-carboxylate.

EXAMPLE 22

Preparation of 6-(1-hydroxyethyl)-3-(2-aminoethyloxy)-1-azabicyclo[3.2.0]hept-2-en-7-one-2-carboxylic acid

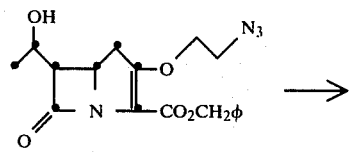 →

-continued

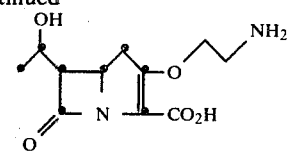

A mixture of benzyl 6-(1-hydroxyethyl)-3-(2-azidoethyloxy)-1-azabicyclo[3.2.0]hept-2-en-7-one-2-carboxylate (25 mg), 10% palladium on powdered charcoal (25 mg), dioxane (3 ml) ethanol (0.25 ml), 1 M dipotassium hydrogen phosphate (0.05 ml), and deionized water (1.75 ml) is hydrogenated at 45 psi for 1 hr. The catalyst is filtered off and washed with 0.1 M pH 7 phosphate buffer (1 ml) and H₂O (1 ml). The combined filtrate is washed with ethyl acetate concentrated in vacuo to ca. 1 ml, and added to a column of Dowex 50-X4 (Na form). The product is eluted with DI H₂O. The appropriate fractions are combined, concentrated in vacuo and lyophilized to provide 6-(1-hydroxyethyl)-3-(2-aminoethyloxy)-1-azabicyclo[3.2.0]hept-2-en-7-one-2-carboxylic acid.

EXAMPLE 23

Following the procedures developed in the foregoing Examples and text, the following representative species of the invention are obtained by analogy. (In the table the symbol "φ" is used for the phenyl radical):

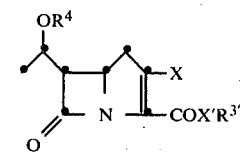

| Compound | $R^4$ | X | X' | $R^{3'}$ |
|---|---|---|---|---|
| 1. | H | Cl | O | Na |
| 2. | H | Br | O | Na |
| 3. | H | OSO₂CH₃ | O | Na |
| 4. | H | OCH₃ | O | Na |
| 5. | H | OCH₂CH₃ | O | Na |
| 6. | H | OCH₂CH₂CH₃ | O | Na |
| 7. | H | OCH₂φ | O | Na |
| 8. | H | OC(O)CH₃ | O | Na |
| 9. | H | OC(O)CH₂φ | O | Na |
| 10. | H | OC(O)CH₂Oφ | O | Na |
| 11. | H | OC(O)CH₂NH₂ | O | H |
| 12. | H | OC(O)CH₂N(CH₃)₂ | O | H |
| 13. | H | OC(O)CH₂N(pyrrolidinyl) | O | H |
| 14. | H | OC(O)CH(NH₂)φ | O | H |
| 15. | H | OC(O)CH(OH)φ | O | Na |

-continued

| Compound | R⁴ | X | X' | R³' |
|---|---|---|---|---|
| 16. | H | OC(O)CH(φ)CO₂Na | O | Na |
| 17. | H | OC(O)φ | O | Na |
| 18. | H | OC(O)—C₆H₄—N(CH₃)₂ | O | Na |
| 19. | H | OC(O)—C₆H₄—CH₂N(CH₃)₂ | O | H |
| 20. | H | OC(O)-(3-pyridyl) | O | H |
| 21. | H | OC(O)—N(tetrazolyl) | O | Na |
| 22. | H | OC(O)CH₂—S—(1-methyltetrazol-5-yl) | O | Na |
| 23. | H | OC(O)CH₂—S—(5-methyl-1,3,4-thiadiazol-2-yl) | O | Na |
| 24. | H | OC(O)N(CH₃)₂ | O | Na |
| 25. | H | OP(O)(N(CH₃)₂)₂ | O | Na |
| 26. | H | Cl | O | CH₂OC(O)—(CH₃)₃ |
| 27. | H | OCH₂CH₂CH₃ | O | CH₂—C₆H₄—O—C₆H₅ |
| 28. | H | OC(O)φ | O | CH₂CH=C(CH₃)₂ |
| 29. | OC(O)CH₃ | OCH₂CH₂CH₃ | O | Na |
| 30. | CH₃ | OCH₂CH₂CH₃ | O | Na |

EXAMPLE 24

Benzyl 1-azabicyclo[3.2.0]heptan-3,7-dione-2-carboxylate

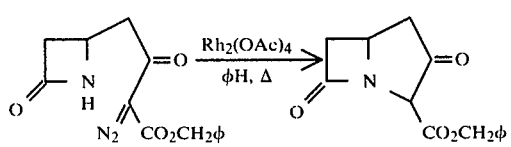

A mixture of 4-(3-benzyloxycarbonyl-3-diazo-2-oxo-propyl)-azetidin-2-one (718 mg. 2.5 mMol), rhodium (II) acetate (5 mg) and anhydrous benzene (50 ml) is deoxygenated by bubbling nitrogen through it for 45 minutes. The mixture is then stirred and heated in an oil bath maintained at 80° C. for 70 minutes. After cooling to room temperature, the mixture is filtered and the filtrate is evaporated under vacuum to an oil. Crystallization from ethyl acetate (5 ml)-diethylether (20 ml) provides benzyl 1-azabicyclo[3.2.0]heptan-3,7-dione-2-carboxylate (502 mg, 77% yield) as small, white prisms:

mp 100°–102°; IR (CH$_2$Cl$_2$) 1770; 1741 cm$^{-1}$; UV (dioxane) 220 nm; NMR (CDCl$_3$, 300 MHz) α2.43 (dd,1,J=8 and 19,H4a), 2.94 (dd,1,J=6.5 and 19,H4b), 2.99 (dd,1,J=2 and 16, H6B), 3.63 (dd,1,J=5 and 16,H6α), 4.18 (m,1,H5), 4.76 (S,1,H2), 5.23 (S,2,CH$_2$φ), and 7.40 (S,5,ArH); MS m/e 259 (M+), 231 (M+ −28), 217 (M+ −42), 203, 187, 186, 168 (M+ −91), 124, and 91.

Anal. Calculated for C$_{14}$H$_{13}$NO$_4$: C, 64.86; H, 5.05; N, 5.40. Found: C, 64.92; H, 5.01; N, 5.11.

EXAMPLE 25

Dicyclohexylammonium 1-azabicyclo[3.2.0]heptan-3,7-dione-2-carboxylate

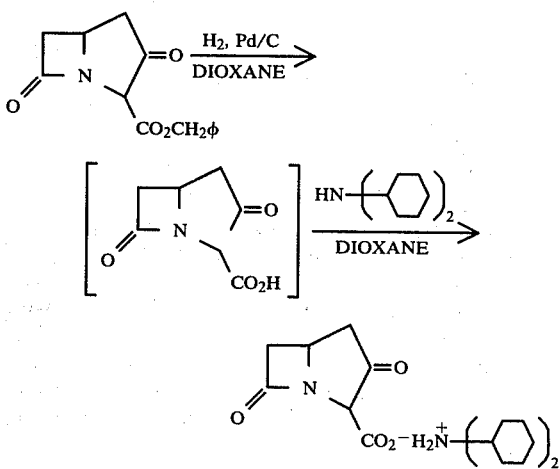

A solution of benzyl 1-azabicyclo[3.2.0]heptan-3,7-dione-2-carboxylate (25.9 mg, 0.1 mMol) in dioxane (1.5 ml) is added to a mixture of 10% palladium on charcoal (5 mg) and dioxane (1.0 ml) which had been equilibrated under an atmosphere of hydrogen for 10 minutes. The resulting mixture is stirred under 1 atmosphere of hydrogen at room temperature for 30 mins., during which time 2.6 ml of hydrogen are absorbed. The mixture is filtered and the catalyst is washed with more dioxane (0.5 ml). The filtrate, which contains 1-azabicyclo[3.2.0]heptan-3,7-dione-2-carboxylic acid, is divided into two equal 1.5 ml portions.

One portion of the dioxane filtrate is treated with a solution of dicyclohexylamine (9.1 mg, 0.05 mMol) in dioxane. The solvent is removed under vacuum and the residue is triturated with diethyl ether to yield dicyclohexylammonium 1-azabicyclo[3.2.0]heptan-3,7-dione-2-carboxylate as a white powder: IR (Nujol) 1764, 1637 cm$^{-1}$; NMR (D$_2$O) α1.1–2.2 (m,—CH$_2$CH$_2$CH$_2$CH$_2$CH$_2$—), 2.64 (dd,J=7.8 and 19.0, H4a), 2.89 (dd, J=7.9 and 19.0, H4b), 3.08 (dd, J=2 and 16.6, H6β), 3.26 (m, N—CH), 3.61 (dd, J=4.7 and 16.6, H6α), 4.17 (m, H5), and 4.8 (br s, HOD, obscures H2 resonance).

EXAMPLE 26

Benzyl 3-(p-toluenesulfonyloxy)-1-azabicyclo[3.2.0]hept-2-2n-7-one-2-carboxylate

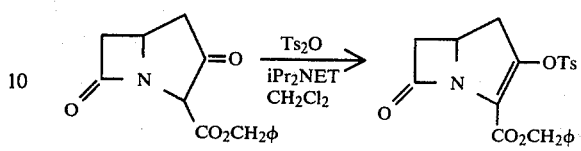

p-Toluenesulfonic anhydride (326 mg, 1 mμol) and N,N-diisopropylethylamine (1.92 μl, 1.1 mμol) are added to an ice-cold, stirring solution of benzyl 1-azabicyclo[3.2.0]heptan-3,7-dione-2-carboxylate (259 mg, 1 mμol) in anhydrous methylene chloride (10 ml). The resulting solution is stirred in the cold and under a nitrogen atmosphere for 2.5 hours. The solution is diluted with methylene chloride (20 ml), washed with water (10 ml). 1 M pH 3 phosphate buffer (10 ml) and 5% aqueous sodium bicarbonate (2×10 ml) dried with magnesium sulfate, filtered, and evaporated under vacuum to a semi-solid. This material is triturated with ice-cold ethyl acetate (2×2 ml) and diethyl ether (2×5 ml) to provide benzyl 3-(p-toluenesulfonyloxy)-1-azabicyclo[3.2.0]hept-2-en-7-one-2-carboxylate (276 mg. 67%) as a white powder. Recrystallization from methylene chloridediethyl ether gives analytically pure product as small white needles: mp 103°–105°; IR (CH$_2$Cl$_2$) 1786, 1723, 1382, and 1190 cm$^{-1}$; NMR (CDCl$_3$) δ 2.44 (s,3,ArCh$_3$) 3.03 (dd,1,J=3.0 and 17.0,HGβ), 3.16 (dd,1,J=8.5 and 18.7,H4a), 3.32 (dd,1,J=10.0 and 18.7,H46), 3.55 (dd,1,J=5.5 and 17.0, HG), 4.21 (m,1,H5), 5.14 (ABq,2,J=12,CH$_2$Ar), 7.35 (S,5,ArH0, 7.26 and 7.75 (two d's,4,J=9,ArH); UV (dioxane) 283 (E6600) and 277 (E6500) nm.

Anal., Calculated for C$_{21}$H$_{19}$NO$_6$S: C, 61.01; H, 4.63; N, 3.39. Found: C, 59.94; H, 4.47; N, 3.26.

EXAMPLE 27

Benzyl 3-(p-nitrobenzenesulfonyloxy)-1-azabicyclo[3.2.0]hept-2-en-7-one-2-carboxylate

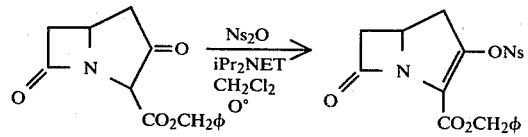

An ice-cold solution of benzyl 1-azabicyclo[3.2.0]heptan-3,7-dione-2-carboxylate (20 mg, 0.077 mmol) in methylene chloride (2 ml) is treated with p-nitrobenzenesulfonic anhydride (37.3 mg, 0.096 mmol) and N,N-diisopropylethylamine (18.3 μl, 0.015 mmol). After stirring in the cold for 20 minutes, the solution is diluted with cold methylene chloride (1 ml) and cold 0.1 M pH 7 phosphate buffer (2 ml) and shaken. The organic phase is separated, washed with cold 0.1 M pH 7 phosphate buffer (2×2 ml), water and brine, dried with magnesium sulfate, and filtered. The filtrate is diluted with cold methanol (0.5 ml) and quickly evaporated under vacuum to give a solid. The crude product is triturated with cold methanol and dried under vacuum to provide benzyl 3-(p-nitrobenzenesulfonyloxy)-1- azabicyclo[3.2.0]hept-2-en-7-one-2-carboxylate (26 mg) as a white solid: mp 86°–88°; IR (CH$_2$Cl$_2$) 1794, 1723, 1521, and 1344 cm$^{-1}$; UV (CHCl$_3$) 257 ($\epsilon$10,600) and 280 ($\epsilon$7,600) nm; NMR (CDCl$_3$) δ3.08 (dd,1,J=3.6 and 17, H6β), 3.25 (dd,1,J=8.8 and 18, H3a), 3.35 (dd,1,J=9.8 and 18,H4b), 3.59 (dd,1,J=5.4 and 17, H6α), 4.26 (m,1,H5), 5.10 (ABq, 2, J=21.2,CH$_2$φ), 7.32 (s,5, C$_6$H$_5$), 8.03 and 8.22 (two d's, 4, J=9.3, NO$_2$C$_6$H$_4$).

Preparation of p-nitrobenzene sulfonic anhydride

A mixture of p-nitrobenzenesulfonic acid (20 g), phosphorous pentoxide (50 g) and 1,2-dichloroethylene (100 ml) is heated at reflux for 4 days. The hot supernatant is decanted from the gummy residue and allowed to cool to room temperature. The resulting crystalline precipitate of p-nitrobenzenesulfonic anhydride (1.5 g) is collected, washed with anhydrous diethylether, and dried under vacuum. The gummy residue is twice more refluxed overnight with 100 ml portions of dichloroethylene and worked up as above to provide additional p-nitrobenzenesulfonic anhydride (4.0 g): mp 171°–172°.

EXAMPLE 28

Benzyl 3-diphenylphosphoryl-1-azabicyclo[3.2.0]hept-2-en-7-one-2-carboxylate

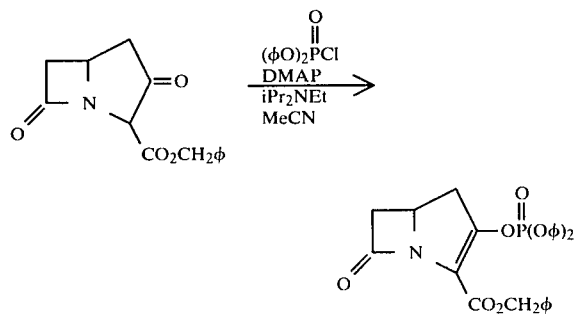

An ice-cold, stirring solution of benzyl 1-azabicyclo[3.2.0]heptan-3,7-dione-2-carboxylate (13 mg, 0.05 mMol), 4-dimethylamine pyridine (1.2 mg, 0.01 mMol) and N,N-diisopropylethylamine (12.2 μl, 0.07 mMol) in anhydrous acetonitrile (0.5 ml) is treated with diphenyl chlorophosphate (12.4 μl, 0.06 mMol). The resulting solution is stirred in the cold and under a nitrogen atmosphere for 2 hours, then diluted with methylene chloride (5 ml), washed with water (2 ml), 0.1 M pH 7 phosphate buffer (2 ml) and brine, dried over magnesium sulfate, and filtered. Evaporation of the filtrate under vacuum leaves crude benzyl 3-diphenylphosphoryl-1-azabicyclo[3.2.0]-hept-2-en-7-one-2-carboxylate (22 mg) as an oil: UV (dioxane) 281 nm; NMR (CDCl$_3$) α2.90 (dd,1,J=3 and 17, H6β), 3.17 (m,2,H4a and H4b), 3.52 (dd,1,J=5.5 and 17,H6α), 4.13 (m,1,H5), 5.28 (S,2,CH$_2$φ), and 7.30 (m,15,ArH).

EXAMPLE 29

N-(t-Butyldimethylsilyl)-4-[3-(p-nitrobenzyloxycarbonyl)-2-hydroxypropyl]-azetidin-2-one

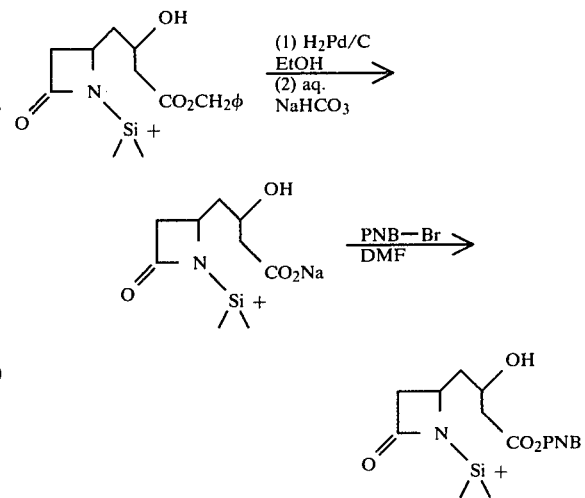

A mixture of crude N-(t-butyldimethylsilyl)-4-(3-benzyloxycarbonyl-2-hydroxypropyl)-azetidin-2-one (11.33 g, 30 mmol), ethanol (300 ml) and 10% palladium on charcoal (1.13 g) is hydrogenated at 50 psi for 1 hour. The mixture is filtered and the filtrate is treated with water (150 ml) containing sodium bicarbonate (2.52 g, 30 mmol) and concentrated under vacuum to ca 100 ml. The aqueous concentrate is washed with ethyl acetate (2×100 ml) and lyophilized to provide the sodium carboxylate (7.70 g) as a white powder.

The sodium salt and p-nitrobenzyl bromide (6.48 g, 30 mmol) are dissolved in anhydrous dimethyl formamide (150 ml) under a nitrogen atmosphere. After standing for 1 hour at room temperature, the solution is evaporated under vacuum to a semi-solid. The residue is taken up in ethyl acetate (200 ml), washed with water (2×200 ml) and brine, dried over magnesium sulfate, filtered, and evaporated under vacuum. The residual yellow oil is chromatographed on silica gel (250 g) using 1:1 toluene:ethyl acetate as eluting solvent to provide N-(t-butyldimethylsilyl)-4-[3-(p-nitrobenzyloxycarbonyl)-2-hydroxypropyl]-azetidin-2-one (8.92 g, 70%) as an oil which solidified on standing: IR (CH$_2$Cl$_2$) 3585, 1733, 1527, and 1350 cm$^{-1}$; NMR (CDCl$_3$) δ 0.22 (s,3,CH$_3$), 0.25 (s,3,CH$_3$), 0.93 (s,9,C(CH$_3$)$_3$), 1.16–2.33 (m,2,CH-CH$_2$-CH), 2.40–3.47 (m,3,OH and H3 and H3β), 2.55 (d,2,J=6,CH$_2$CO$_2$), 3.50–4.33 (m,2,H4 and CH—OH), 5.30 (s,2,CH$_2$Ar), and 7.55, 8.27 (two d's,4,J=8.5,ArH).

EXAMPLE 30

N-(t-Butyldimethylsilyl)-4-[3-(p-nitrobenzyloxycarbony)-2-hydroxypropyl]-azetidin-2-one

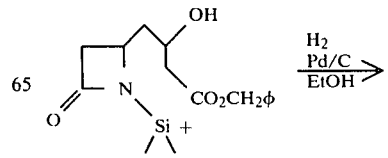

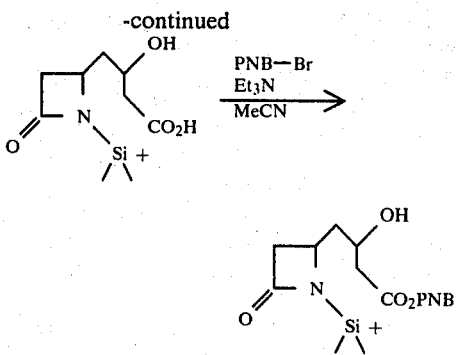

A mixture of crude N-(t-butyldimethylsilyl)-4-(3-benzyloxycarbonyl-2-Hydroxypropyl)-azetidin-2-one (13.46 g, 35.6 mmol), 10% palladium on charcoa, and ethanol (200 ml) is hydrogenated at 40 psi for 30 mins. The mixture is filtered and the filtrate is evaporated under vacuum and stripped with toluene to give N-(t-butyldimethylsilyl)-4-(3-carboxy-2-hydroxypropyl)-azetidin-2-one (9.51 g) as an off-white solid: IR (neat film from $Me_2CO$) 3200 (br), 1735, and 1700 (shifts to 1590 with $Et_3N$) $cm^{-1}$; NMR ($Me_2CO$-$d_6$) δ 0.25 (s,6,2$CH_3$), 0.98 (s,9,C($CH_3$)$_3$) 1.17–2.33 (m,2,CH-C$\underline{H}_2$-CH), 2.50 (d,2,J=6.5, $CH_2CO_2$), 2.50–3.40 (m,2,H3 and H3β), 3.97 (m,2,H4 and C$\underline{H}$OH); MS on bistrimethylsilyl derivative m/e 431 (M+), 416 (M+ −57) and 332 (374-42).

The crude carboxylic acid is suspended in anhydrous acetonitrite (150 ml) and treated with p-nitrobenzyl bromide (7.56 g, 35 mμol) and triethylamine (4.9 ml, 35 mμol). The resulting solution is kept at room temperature for 2 days and then in a refrigerator for 3 days. The reddish orange solution is evaporated under vacuum and the residue shaken with ethyl acetate (100 ml, 2×50 ml) and filtered to remove triethylammonium bromide. The ethyl acetate filtrate is washed with water (3×100 ml) and brine, dried with magnesium sulfate, filtered, and evaporated under vacuum to an amber oil (13.62 g). Crystallization from diethyl ether affords N-(t-butyldimethylsilyl)-4-[3-(p-nitrobenzyloxycarbonyl)-2-hydroxypropyl]azetidin-2-one (6.84 g) as an off-white powder. Chromatography of the mother liquors on a silica gel column using 1:1 toluene-ethyl acetate as eluting solvent affords addition product (3.14 g) as an oil which solidifies.

EXAMPLE 31

N-(t-Butyldimethylsilyl)-4-[3-(p-nitrobenzyloxycarbonyl)-2-oxopropyl]-azetidin-2-one

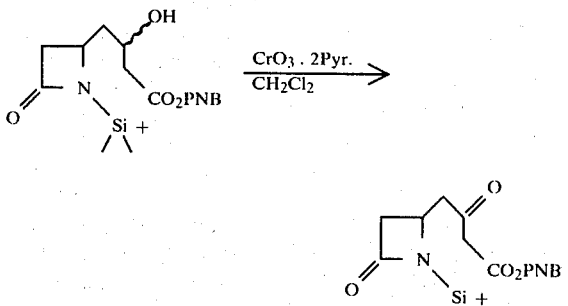

Anyhdrous chromium trioxide (16.88 g 169 mmol) is added to a solution of anhydrous pyridine (27.3 ml, 338 mmol) in anhydrous methylene chloride (470 ml). The resulting mixture is stirred at room temperature for 30 minutes and then treated with a solution of N-(t-butyldimethylsilyl)-4-[3-(p-nitrobenzyloxycarbonyl)-2-hydroxypropyl]-azetidin-2-one (8.92 g, 21.1 mmol) in methylene chloride (80 ml). The reaction mixture is stirred an additional 15 minutes at room temperature and then treated with 2-propanol (6.75 ml). The methylene chloride phase is decanted from the dark, tary residue and evaporated under vacuum. The residue from this operation is triturated with diethyl ether (350 ml) and filtered through a pad of magnesium sulfate which is washed with additional ether (150 ml). The ethereal filtrate is washed with water (200 ml), 5% aqueous sodium bicarbonate (200 ml) and brine, dried with magnesium sulfate, filtered, evaporated under vacuum, and stripped with toluene to afford the crude product (5.99 g) as an amber oil. Chromatigraphy on a silica gel column using 3:2 petroleum etherethyl acetate as eluting solvent yields N-(t-butyldimethylsilyl)-4-[3-(p-nitrobenzyloxycarbonyl)-2-oxopropyl]-azetidin-2-one (5.17 g, 58%) as a pale yellow, viscous oil which solidifies. Trituration with diethyl ether gives the product as small, white crystals: mp 65°–66.5°, IR ($CH_2CL_2$) 1732, 1522, and 1350 cm) NMR ($CDCl_3$) δ 0.20 (s,3,$CH_3$), 0.23 (s,3,$CH_3$), 0.93 (s,9,C($C\underline{H}_3$)$_3$), 2.58 (dd,1,J=2.7 and 15.7, H3β), 2.72 (dd,1,J=9.4 and 18.2, C$\underline{H}_2$COC$H_2$CO$_2$), 3.19 (dd,1,J=4.0 and 18.2, C$\underline{H}_2$COC$H_2$CO$_2$), 3.35 (dd,1,J=5.3 and 15.7,H3α), 3.55 (s,2,COC$H_2$CO$_2$), 3.90 (m,1,H4), 5.30 (s,2,$CH_2$Ar), 7.55 and 8.25 (two d$^{15}$,4,J=8.5, ArH); MS m/e 405 (M+ −15), 363 (M+ −57), 321 (363-42) and 136.

Anal, Calculated for $C_{20}H_{28}N_2O_6Si$: C,57.12; H,6.71; N,6.66. Found: C,57.28; H,6.75; N,6.60.

EXAMPLE 32

4-[3-(P-Nitrobenzyloxycarbonyl)-2-Oxopropyl]Azetidin-2-One

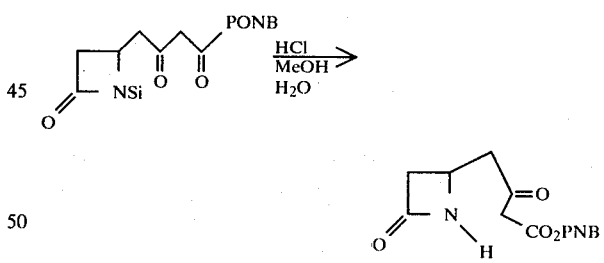

A solution of N-(t-butyldimethylsilyl)-4-[3-(p-nitrobenzyloxycarbonyl)-2-oxopropyl]-azetidin-2-one (5.17 g, 12.3 mMol) in methanol (55 ml) is treated with 1 N hydrochloric acid (6.2 ml) and then kept at room temperature for 200 mins. The solution is treated with 1 M dipotassium hydrogenphosphate (6.2 ml) and concentrated under vacuum. The residue is taken up in ethyl acetate (100 ml), washed with brine, dried over magnesium sulfate, filtered, and evaporated under vacuum. Triturating the resulting oil with diethyl ether yields 4-[3-(p-nitrobenzyloxycarbonyl)-2-oxopropyl]-azetidin-2-one (3.42 g, 91%) as an off-white powder: mp 50°–52°; IR ($CH_2Cl_2$) 3416, 1767, 1723, 1528, and 1352 $cm^{-1}$; NMR ($CDCl_3$) α2.60 (ddd,1,J=1,2.7, and 15.1,H3β), 2.77 (dd,1,J=8.4 and 18.2, CHC$\underline{H}_2$CO), 3.13 (dd,1,J=5.1 and 18.2, CHC$\underline{H}_2$CO), 3.20 (ddd,1,J=2.4, 5.0, and 15.1 H3α), 3.57 (s,2,COCH₂CO₂), 3.98 (m,1,H4); 5.27 (s,2,CH₂Ar), 6.28 (or s,1,NH), 7.53 and 8.23 (two d's,4,J=8.5, ArH); mass spectrum m/e 306(M+), 264(M+ −42), 237, 153, 125, 111, and 136.

EXAMPLE 33

4-[3-(P-Nitrobenzylorycarbonyl)-3-Diazo-2-Oxo-propyl]-Azetidin-2-One

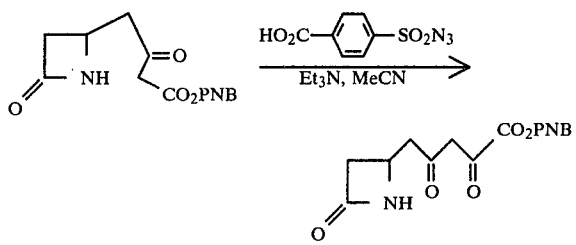

p-Carboxybenzyenesulfonylazide (2.67 g, 11.8 mMol) and triethylamine (4.68 ml, 33.6 mMol) are added to an ice-cold, stirring solution of 4-[3-(p-nitrobenzyloxycarbonyl)-2-oxopropyl]-azetidin-2-one (3.42 g, 11.2 mMol) in anhydrous acetonitrile (70 ml). The resulting mixture is stirred in the cold for 10 minutes and at room temperature for 60 minutes. The mixture is diluted with ethyl acetate (200 ml) and filtered. The filtrate is washed with water (2×100 ml), 1 M pH3 phosphate buffer (50 ml), 0.1 M pH7 phosphate buffer (100 ml), and brine, dried over magnesium sulfate, filtered, and evaporated under vacuum to a yellow foam (3.75 g). The crude product is taken up in methylene chloride (ca. 10 ml), heated briefly with activated charcoal, and filtered through a pad of magnesium sulfate. The filtrate is diluted with diethyl ether (ca. 40 ml) and scratched to yield a precipitate. The precipitate is collected, washed with ether, and dried under vacuum to provide 4-[3-(p-nitrobenzyloxycarbonyl)-3-diazo-2-oxopropyl]azetidin-2-one (3.29 g, 88%) as a pale yellow powder: mp 114.5°–116.5°; IR (CH₂Cl₂) 3413, 2142, 1767, 1724, 1657, 1530, and 1352 cm⁻¹; NMR (CDCl₃) α2.68 (ddd,1,J=1.2, 2.7, and 14.8, H3β), 3.02 (dd,1,J=8.4 and 18.0, CHCH₂CO), 3.22 (ddd,1,J=2.4, 4.8, and 14.8, H3α); 343 (dd,1,J=4.6 and 18.0, CHCH₂CO), 4.00 (m,1,H4), 5.38 (s,2,CH₂Ar), 6.30 (brs,1,NH), 7.57 and 8.27 (two d's,4,J=8.5, ArH); mass spectrum m/e 332(M+), 304(M+ −28), 290(M+ −42), 262, and 263.

Anal., calculated for C₁₄H₁₂N₄O₆: C,50.61; H,3.64; N,16.86. Found: C,50.34; H,3.42; N,16.72.

EXAMPLE 34

P-Nitrobenzyl 1-Azabicyclo[3.2.0]Heptan-3,7-Dione-2-Carboxylate

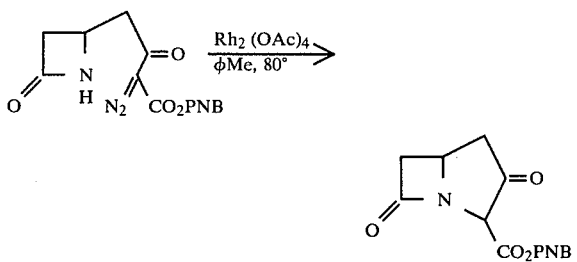

A suspension of 4-[3-(p-nitrobenzylocycarbonyl)3-diazo-2-oxopropyl]-azetidin-2-one(2.93 g) and rhodium (II) acetate (15 mg) in anhydrous toluene (300 ml) is degassed by bubbling nitrogen through it for 60 minutes. The mixture is then stirred and heated in an oil bath maintained at 80° C. After a few minutes, the diazo compound dissolves and gas evolution commences. The mixture is heated at 80° C. for 100 minutes, then allowed to stand at room temperature for 30 mins. before filtering through a pad of celite. The filtrate is evaporated under vacuum to an oily residue which is triturated with diethyl ether to afford p-nitrobenzyl 1-azabicyclo[3.2.0]heptan-3,7-dione-2-carboxylate (2.53 g, 94%) as an off-white powder. Recrystallization from ether provides analytically pure product: mp 127°–128°: IR (CH₂Cl₂) 1776, 1753, 1529, and 1352 cm⁻¹; NMR (CDCl₃) α2.47 (dd,1,J=8.2 and 18.8, H4a), 2.98 (dd,1,J=6.8 and 18.8, H4b), 3.00 (dd,1,J=2.0 and 12.0, H6β), 3.70 (dd,1,J=4.8 and 12.0, H6α), 4.20 (m,1,H5), 4.80 (s,1,H2), 5.32 (s,2,CH₂Ar), 7.57 and 8.25 (two d's,4,J=8,ArH); mass spectrum m/e 304(m+), 276(M+ −28), 262 (M+ −42), and 168(M+ −136).

Anal., calculated for C₁₄H₁₂N₂O₆: C,55.27; H,3.98; N,9.21. Found: C,55.06; H,4.03; N,8.99.

EXAMPLE 35

P-Nitrobenzyl 3-(p-Toluenesulfonyloxy)-1-azabicyclo[3.2.0]hept-2-en-7-one-2-carboxylate

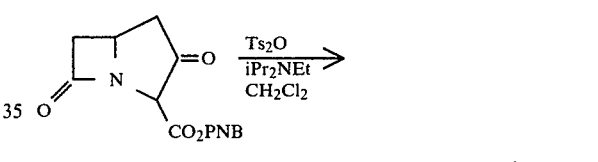

p-toluenesulfonic anhydride (520 mg, 1.59 mµol) and N,N-diisopropylethylamine (300 µl, 1.72 mµol) are added to an ice-cold, stirring solution of p-nitrobenzyl 1-azabicyclo[3.2.0]heptan-3,7-dione-2-carboxylate (484 mg, 1.59 mµol) in anhydrous methylene chloride (17 ml). The resulting solution is stirred in the cold for 2 hours, then diluted with more methylene chloride, washed with water, 1 µph 3.4 phosphate buffer and saturated aqueous sodium bicarbonate, dried with magnesium sulfate, filtered, and evaporated under vacuum. Addition of cold ethyl acetate and a few seed crystals to the oily residue induces crystallization. The product is collected, washed with cold ethyl acetate, and dried under vacuum to afford p-nitrobenzyl 3-(p-toluenesulfonyloxy)-1-azabicyclo[3.200]hept-2-en-7-one-2-carboxylate (446 mg, 61%) as off-white crystals: mp 99°–102° (dec.); IR (neat) 1790, 1725, 1521, 1345, and 1172 cm⁻¹; UV (CH₂Cl₂) 272 nm; NMR (CDCl₃) δ 2.40 (s,3,ArCH₃), 3.06 (dd,1,J=3.0 and 17.2 HGβ), 3.16 (dd,1,J=9.0 and 9.0,H4a), 3.31 (dd,1,J=9.0 and 10.0, H46), 3.59 (dd,1,J=5.8 and 17.2, HG), 4.24 (m,1,H5), 5.20 and 5.32 (ABq,2,J=14.0,CH₂Ar), 7.32 and 7.77 (two d's,4,J=8.0, p-MeC₆H₄), 7.51 and 8.19 (two d's,4,J=8.0,p-NO₂C₆H₄).

EXAMPLE 36

Benzyl 3-methoxy-1-azabicyclo[3.2.0]hept-2-en-7-one-2-carboxylate

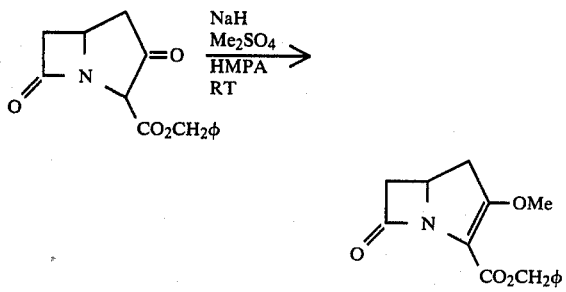

A solution of benzyl 1-azabicyclo[3.2.0]heptan-3,7-dione-2-carboxylate (25.9 mg, 0.1 mMol) in anhydrous hexamethylphosphoramide (1.0 ml) is cooled in an ice-bath and stirred under a nitrogen atmosphere. Dimethyl sulfate (11.4 μl, 0.12 mMol) and 57% sodium hydride in mineral oil (5.0 mg, 0.12 mMol) are added to the solution. The cooling bath is removed and the resulting mixture is stirred at room temperature for 60 minutes. The mixture is diluted with ethyl acetate (10 ml) and water (20 ml), shaken, and the layers separated. The organic layer is washed with water (3×5 ml) and brine, dried with magnesium sulfate, diluted with toluene (10 ml), and evaporated under vacuum to an oil. This material is chromatographed on a 0.25 mm×10×20 cm silica gel GF plate using 3:1 toluene-ethyl acetate as developing solvent. The major UV visible band at $R_f$ 0.1 was removed and eluted with ethyl acetate to provide benzyl 3-methoxy-1-azabicyclo[3.2.0]hept-2-en-7-one-2-carboxylate (5.6 mg) as a clear oil: IR ($CH_2Cl_2$) 1775 and 1700 cm$^{-1}$; UV (EtOAc) 288 nm; NMR (CDCl$_3$) $\delta$2.87 (dd,1, J=2.8 and 16, H6$\beta$), 3.03 (m,2,H4a and H4b), 3.50 (dd,1, J=5.5 and 16, H6$\alpha$), 3.80 (m,1, H5), 3.92 (s,3,CH$_3$), 5.28 (s,2,CH$_2$$\phi$), and 7.40 (m,5,C$_6$H$_5$); mass spectrum m/e 273 (M+) and 231 (M+ −42).

This product is also obtained by treating the bicyclo keto ester with dimethyl sulfate and excess potassium carbonate in hexamethylphosphoramide or dimethylformamide.

EXAMPLE 37

Preparation of Pharmaceutical Compositions

One such unit dosage form comprises 120 mg of 6-(1'-hydroxyethyl)-3-aminoethyloxy-1-azabicyclo[3.2.0]-hept-2-en-7-one-2-carboxylic acid with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more then 145 mg of ingredients together, larger capsules such as compressed tablets and pills can also be prepared. The following examples are illustrative of the preparation of pharmaceutical formulations:

| TABLET | PER TABLET |
| --- | --- |
| 6-(1'-hydroxyethyl)-3-amino-ethyloxy-1-azabicyclo [3.2.02hept-2-en-7-one-2-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
| --- | --- |
| Ampoule: | |
| 6-(1'-hydroxyethyl)-3-aminoethyloxy-1-azobicylo [3.2.0]hept-2-en-7-one-2-carboxylic acid | 500 mg. |
| OPTHALMIC SOLUTION | |
| 6-(1'-hydroxyethyl)-3-aminoethyloxy-1-azabicyclo [3.2.0]hept-2-en-7-one-2-carboxylic acid | 100 mg. |
| Hydroxypropylmethyl | 5 mg. |
| Sterile Water to | 1 ml. |
| OTIC SOLUTION | |
| 6-(1'-hydroxyethyl)-3-aminoethyloxy-1-azabicyclo [3.2.0]hept-2-en-7-one-2-carboxylic acid | 100 mg. |
| Benzalkonium chloride | 0.1 mg. |
| Sterile Water to | 1 ml. |
| TOPICAL OINTMENT | |
| 6-(1'-hydroxyethyl)-3-aminoethyloxy-1-azabicyclo [3.2.0]hept-2-en-7-one-2-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients, as for example, with other antibacterial agents such as lincomycin, a penicillin, streptomycin, nonobiocin, genatmicin, neomycin, colistin and kanamycin, or with other therapeutic agents such as probenecid.

What is claimed is:

1. A compound having the structural formula:

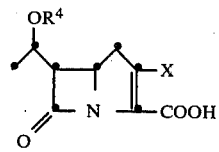

and the pharmaceutically acceptable salt derivatives thereof wherein: $R^4$ is hydrogen; and X is chloro, bromo, oxygen (when X is oxygen, the 2-3 bond is saturated), or —OR wherein R is selected from the group consisting of substituted and unsubstituted alkyl, having 1-6 carbon atoms, cycloalkyl and cycloalkylalkyl wherein the ring moiety comprises 3-6 carbon atoms and the alkyl comprises 1-4 carbon atoms, aralkyl having from 7-16 carbon atoms and acyl wherein acyl is selected from the group consisting of $$\overset{O}{\underset{\|}{C}}CH_3,$$

$$\overset{O}{\underset{\|}{C}}CH_2NH_2,$$

$$\overset{O}{\underset{\|}{C}}CHNH_2,$$
$$\qquad\ \ |$$
$$\qquad\ \ \phi$$

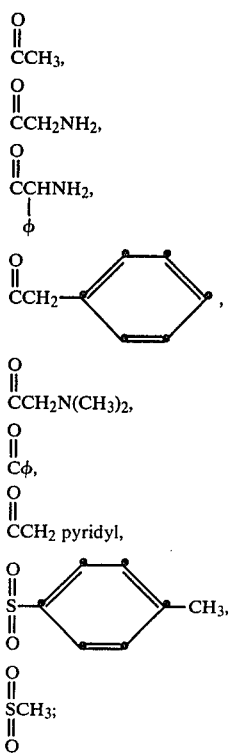

$$\overset{O}{\underset{\|}{C}}CH_2N(CH_3)_2,$$

$$\overset{O}{\underset{\|}{C}}\phi,$$

$$\overset{O}{\underset{\|}{C}}CH_2\,pyridyl,$$

wherein the substituent or substituents on the radical R are selected from: amino or monoalkylamino wherein the alkyl has 1–6 carbon atoms.

2. A compound according to claim 1 wherein R is selected from the group consisting of:

$$\overset{O}{\underset{\|}{C}}CH_3,$$

$$\overset{O}{\underset{\|}{C}}CH_2NH_2,$$

$$\overset{O}{\underset{\|}{C}}CHNH_2,$$
$$\qquad\ \ |$$
$$\qquad\ \ \phi$$

-continued

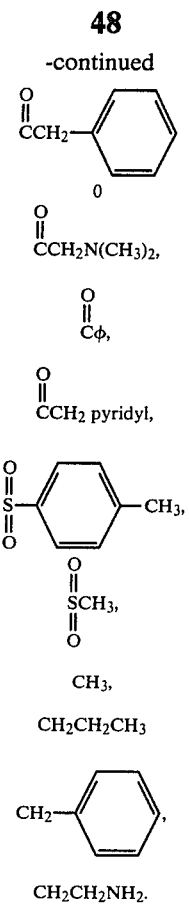

CH$_3$,

CH$_2$CH$_2$CH$_3$

CH$_2$CH$_2$NH$_2$.

3. A compound having the structure:

[structure with OH, N, COOR, and β-lactam ring shown]

wherein R is hydrogen or a pharmaceutically acceptable salt cation.

4. An antibiotic pharmaceutical composition comprising a therapeutically effective amount of a compound according to claim 1 and a inert pharmaceutical carrier therefor.

* * * * *